United States Patent
Reshetnikov et al.

(10) Patent No.: US 7,550,587 B2
(45) Date of Patent: Jun. 23, 2009

(54) PHOTOSENSITIZER AND METHOD FOR PRODUCTION THEREOF

(75) Inventors: Andrei Valentinovich Reshetnikov, Moscow (RU); Igor Dmitrievich Zalevsky, Fryazino (RU); Jury Viktorovich Kemov, Chernogolovka (RU); Andrei Valentinovich Ivanov, Moscow (RU); Artashes Vacheevich Karmenyan, Moscow (RU); Alexandr Tikhonovich Gradjushko, Moscow (RU); Vladimir Petrovich Laptev, Monino (RU); Nataliya Petrovna Neugodova, Moscow (RU); Olga Yurievna Abakumova, Istra (RU); Valery Alexeevich Privalov, Chelyabinsk (RU); Alexandr Vladimirovich Lappa, Chelyabinsk (RU); Vladimir Alexandrovich Romanov, Khimki (RU)

(73) Assignee: Obschestvo S Ogranichennoi Otvetstvennostiju "Rada-Pharma" (RU)

( * ) Notice: Subject to any disclaimer, the term of this patent is extended or adjusted under 35 U.S.C. 154(b) by 542 days.

(21) Appl. No.: 11/171,076

(22) Filed: Jun. 30, 2005

(65) Prior Publication Data

US 2006/0003983 A1 Jan. 5, 2006

Related U.S. Application Data

(63) Continuation of application No. 10/473,445, filed as application No. PCT/RU01/00399 on Oct. 4, 2001, now Pat. No. 6,969,765.

(30) Foreign Application Priority Data

Mar. 30, 2001 (RU) .............................. 2001108397

(51) Int. Cl.
C07B 47/00 (2006.01)
C07D 487/22 (2006.01)
(52) U.S. Cl. ............................................. 540/145
(58) Field of Classification Search ................. 540/145
See application file for complete search history.

(56) References Cited

U.S. PATENT DOCUMENTS 5,216,012 A 6/1993 Morgan et al.
5,330,741 A 7/1994 Smith et al.

FOREIGN PATENT DOCUMENTS

RU 2054476 C1 7/1994
RU 2152790 C1 7/2002

OTHER PUBLICATIONS

Derwent Abstract of Patent RU 2 054 476 C1, *Derwent Publications Ltd.*, Accession No. 1996-463143, 1996.

(Continued)

*Primary Examiner*—James O. Wilson
*Assistant Examiner*—Paul V. Ward
(74) *Attorney, Agent, or Firm*—Brinks Hofer Gilson & Lione; G. Peter Nichols

(57) ABSTRACT

The invention relates to medicine and concerns a photosensitizer for detecting and curing tumors. The inventive photosensitizer is embodied in the form of a composition containing chlorin in the form of salt and alkali metals. The chlorin is composed of 80-90% of chlorin $e_6$, 5-20 of purpurin 5 and the rest being purpurin 18-chlorin $p_6$. Said photosensitizer is produced by extracting *Spirulina* biomass with the aid of acetone. Afterwards said biomass is exposed to acid treatment, neutralization, hydrolysis, extraction of pheophorbide a, dissolution in acetone, addition of a strong base, neutralization and reprecipitation of chlorin $e_6$.

1 Claim, 18 Drawing Sheets

OTHER PUBLICATIONS

Fischer, H. et al., "Chlorophyll. LXXXVII. Partial Oxidation of Several Chlorophyll Derivatives", *Chemical Abstracts Service*, Accession No. 1939-44413, 1939.

Hynninen, P., "Chlorophylls, IV. Preparartion and Purification of Some Derivatives of Chlorophylls a and b", *ACTA Chemica Scandinavica*, vol. 27, No. 5, pp. 1771-1780, 1973.

Iwai, K. et al., "Therapeutic Effect of Chlorin e6 Sodium as a New Photosensitizing Agent in the Photodynamic Therapy of Mouse Tumors", *Journal of Clinical Biochemistry and Nutrition*, vol. 6, No. 2, pp. 117-125, 1989.

Reshetnickov, A. et al., "Novel Drug Form of Chlorin e6", *Proceedings of Spie-the International Society for Optical Engineering, 3909 (Optical Methods for Tumor Treatment and Detection: Mechanisms and Techniques in Photodynamis Therapy IX)*, pp. 124-130, 2000.

Supplementary European Search Report dated Oct. 13, 2005.

PHOTOSENSITIZER AND METHOD FOR PRODUCTION THEREOF

This application claims is a continuation of U.S. Ser. No. 10,473,445 filed Mar. 15, 2004 now U.S. Pat. No. 6,969,765, which claims priority to PCT application Ser. No. PCT/RU01/00399 filed Oct. 4, 2001 and published in Russian on Oct. 10, 2002, as PCT WO 02/078694 A1, and to Russian application No. 2001108397 filed on Mar. 30, 2001, the entire contents of all are incorporated herein by reference.

DESCRIPTION

The invention concerns the sphere of medicine, particularly the sphere of photodynamic therapy (PDT) with the use of biologically active compounds.

Photosensitizers (PS) are used as therapeutic agents at PDT and as fluorescent labels at photodynamic diagnostics (PDD).

Mono-L-aspartil chlorin $e_6$ tetrasodium salt "Npe6" is known as PS (U.S. Pat. No. 4,977,177):

This PS is active at PDT.

Its disadvantages are: the laboriousness of producing, too high-speed tumour accumulation and excretion dynamics, that reduces the time of effective exposure on the tumour, and comparatively low extent of accumulation in malignant formation (tumour) because of high hydrophily, that activates only one of several possible mechanisms of tumour destruction in the PDT process, namely only the blood vessel affection.

Lysil chlorin $p_6$ trisodium salt "LCP" is known as PS (U.S. Pat. No. 5,330,741):

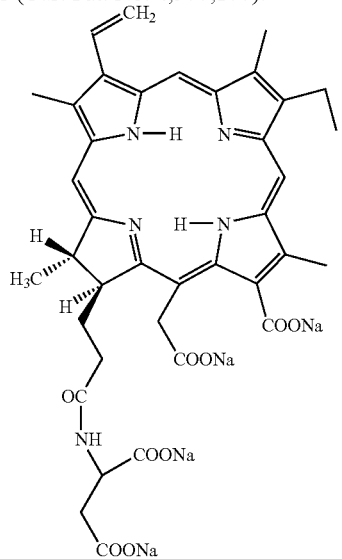

This PS is active at PDT.

Its disadvantages are: the laboriousness of producing and the fact that it is a mixture of two monoamides at 13 and 15 positions in the ratio of 10:1, that may lead to ambiguous biodistribution and excretion.

Pheophorbide a sodium salt is known as PS (U.S. Pat. No. 5,378,835):

This PS can selectively accumulate in malignant tumours and is active at PDT.

Its disadvantage is the tendency to oxidation (chemical instability) at storage as a solution, not full solubility in water after storage as a solid, hydrophoby and, as a consequence, slow excretion out of the organism, that leads to prolonged photosensitivity of skin integument.

Chlorin $e_6$ derivatives are also known as PS (U.S. Pat. No. 5,002,962):

wherein R=hydrophobic hydrocarbon substituent, saturated or unsaturated, straight or branched, consisting of 4 to 25 carbon atoms.

PS, wherein R is hexyl, is tropic to malignant tumours and is an effective agent for PDT.

Its disadvantages are: the laboriousness of preparative producing and purification, high hydrophoby and, as a consequence, slow accumulation in tumour and low stability of water solutions of medicinal forms at storage.

There known a method of producing PS, namely, composition of chlorins as salts with alkaline metals, destined for medical practice. This method consists of the following: plant (floral) biomass are extracted with a 2:1 to 8:1 mixture of hydrocarbon consisting of 6-12 carbon atoms and alcohol consisting of 2-10 carbon atoms, resulting chlorophyll solution is evaporated at the atmospheric pressure, alcohol consisting of less carbon atoms than extraction alcohol is added, hydrocarbon is fully distilled off the mixture at the atmospheric pressure, alcohol alkaline solution is slowly (gradually) added to the alcohol chlorophylls solution at the alcohol boiling temperature, but less than 120° C., till pH is 11.5-11.8, the mixture is cooled, incubated for 4 hours, filtrated, extracted with hydrocarbon consisting of 6-12 carbon atoms, alcohol phase containing magnesium complexes of chlorins is separated, alcohol is evaporated at the atmospheric pressure, hydrochloric acid is added to the residue till pH is 3.5, the mixture is incubated till the end of chlorin precipitation and filtrated, the precipitate is dissolved in methanol, alcohol alkaline solution is added till pH is 8.5, the PS solution is filtrated and evaporated in vacuum (U.S. Pat. No. 3,102,891).

The disadvantages of this method are: the use of high temperatures while removing solvents out of extract, the use of alcohols, especially methyl alcohol, that leads to the allomerisation of E exocycle and formation of multiple different oxidation products of pheophytins and pheophorbides (K. Hyvarinen, J. Helaja, P. Kurchen, I. Kipelainen, P. H. Hynninen. H-1 and C-13 NMR spectra of the methanolic allomerization products of 13(2)-(R)-chlorophyll a. // Magnetic Resonance in Chemistry. -1996.-V. 33.-N8.-p. 646-656), this leading to the complex mixture the composition of which is undefined and hard to reproduce.

There known a method of producing PS, namely, chlorin $e_6$ sodium salt, consisting of the following: 1N NaOH solution is added to the chlorin $e_6$ trimethyl ether solution in tetrahydrofuran, the mixture is stirred for 2 days at the room temperature under nitrogen, water is added to the mixture, then organic solvent is extracted with methylene chloride, the traces of the latter are eliminated by bubbling nitrogen through the chlorin $e_6$ salt solution (U.S. Pat. No. 5,002,962).

The disadvantages of this method are: low availability of sufficient amounts of starting chlorin $e_6$ trimethyl ether, long duration of producing the PS due to chemical inertness of ester radical at the $13^{th}$ position of tetrapyrrole macrocycle and instability of PS medicinal forms at storage in the form of water solution due to incomplete saponification of ester group at the $13^{th}$ position of the macrocycle.

There known a method of producing PS, namely, "LCP" photosensitizer for photodynamic therapy (trisodium salt of lysyl-chlorin $p_6$), consisting of the following: biomass is treated with acetone 2-3 times in order to extract chlorophyll a, the biomass is filtrated or centrifuged, the extract is evaporated, treated with acid in order to remove magnesium ion out of the chlorophyll molecule and to hydrolyse phytyl ester group, methyl alcohol being added for concurrent esterification, the reaction mass is treated with water, pheophorbide a derivative is extracted with chlorous methylene, the extract is neutralised, washed with water, evaporated, chromatographed on aluminium oxide, methylpheophorbide a is crystallised out of the mixture of chlorous methylene-methanol and the resulting pheophorbide a derivative is reacted with strong inorganic base in the presence of oxygen in pyridine-diethyl ether-n-propanol, the reaction mass is treated with water, the water phase is acidified till pH 4, "unstable chlorin" is extracted with chlorous methylene, the extract is evaporated, "unstable chlorin" is redissolved in tetrahydrofurane, the solution is evaporated, this procedure is repeated till absorption at 700 nm stops to increase, the resulting purpurin 18 is dissolved in tetrahydrofurane, esterified with diazomethane, the purpurin 18 methyl ester is mixed with lysine water solution in chlorous methylene in the presence of pyridine, the mixture is stirred for 12 hours at room temperature, the solvents are removed in high vacuum, then the resulting crude product is purified by reverse phase high-performance liquid chromatography (HPLC), the solvents are removed by lyophilisation, the PS is dissolved in phosphate buffer in order to obtain injection solution for PDT, 0.1N NaOH solution is added, pH is adjusted to physiological value of pH 7.35 with 0.1N HCl and the solution is filtrated through microporous filter (U.S. Pat. No. 5,330,741).

The disadvantages of this method are: low reproducibility, labouriousness (the use of high vacuum, crystallization, column chromatography and HPLC, long duration of the reaction with lysine), the use of high toxic and inflammable reagents (diazomethane, pyridine, methanol, tetrahydrofurane, diethyl ether). These disadvantages make the method unsuitable for pharmacetical industry. Besides, the resulting water soluble target product is stable only for 24 hours at 4° C. in the dark in the form of water solution, and in the form of solid substance it is stable only for 4 months at 4° C. in the dark, while according to the pharmacopoeia requirements it should be stable not less than for 6 months (Leach M. W., Higgins R. J., Boggan J. E., Lee S.-J., Autry S., Smith K. M. Effectiveness of a Lysylchlorin $p_6$/Chlorin $p_6$ mixture in Photodynamic Therapy of the Subcutaneous 9L Glioma in the Rat. Cancer Research 1992, V. 52, 1235-1239). Moreover, as for the chemical composition, this PS represents the mixture of monoamides at the $13^{th}$ and $15^{th}$ positions in the approximate ratio of 10:1 that may lead to its ambiguous biological distribution and excretion out of the organism.

The aim of this invention is to obtain PS that is characterised by easy preparative isolation go and purification, balanced hydrophoby-hydrophily and, as a consequence, by the optimal speed of tumour accumulation and excretion out of the tumour and the whole organism, and also by medicinal forms water solutions high stability at storage.

This aim is achieved by producing PS comprising chlorin in the form of salt with alkali metal, chlorin being composed of chlorin $e_6$ (13-carboxy-17-[2-carboxyethyl]-15-carboxymethyl-17,18-trans-dihydro-3-vinyl-8-ethyl-2,7,12,18-tetramethylporphyrin)

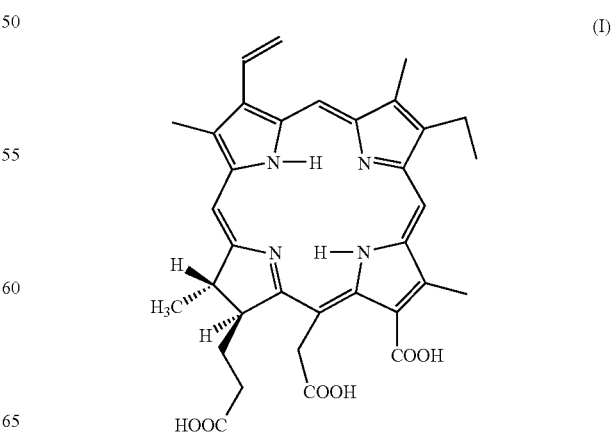

(I)

making up 80-90% purpurin 5 (13-carboxy-17-[2-carboxy-ethyl]-15-formyl-17,18-trans-dihydro-3-vinyl-8-ethyl-2,7,12,18-tetramethylporphyrin)

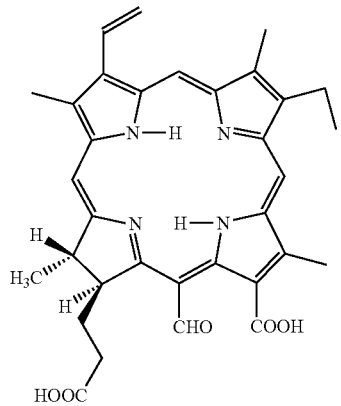

(II)

making up 5-20%, and purpurin 18-chlorin $p_6$ (13-carboxy-17-[2-carboxyethyl]-15-carboxy-17,18-trans-dihydro-3-vinyl-8-ethyl-2,7,12,18-tetramethylporphyrin)

making up the rest, so that mentioned components form the composition, sodium and potassium may be used as alkali metal.

Also the aim of this invention is to achieve high reproducibility of the method of producing PS, its simplicity, chemical stability of the PS medicinal forms not less than for 1 year, as well as to achieve totality of physicochemical and biological properties of PS that provide the effectiveness of the PS at PDT, and also to avoid the use of toxic reagents.

The essence of the suggested method of producing PS is following: *Spirulina* biomass is treated with acetone till chlorophyll a is completely extracted, the biomass is filtered out or centrifuged, the extract is treated with acid in order to remove magnesium ion out of the chlorophyll molecule, the extract is neutralised and precipitated pheophytin a is filtered out, then pheophytin a is hydrolysed in the mixture of hydrochloric acid-acetone-hexane, 6-16 ml acetone, 0.6-6-ml hexane and 5-10 ml concentrated hydrochloric acid being used for every 1 g of crude pheophytin a, the mixture is heated up to 40-60° C. and stirred for 20 min-1 hour, then hexane (6-16 ml) is added and organic phase is washed with the mixture of acetone and hydrochloric acid (2-10:1), water phase is washed with hexane, then water phase containing pheophorbide a is neutralised with excess of sodium citrate (tri-, di- or mono-substituted) water solution, precipitated pheophorbide a is filtered out, washed with water, recrystallised out of the acetone-water mixture, air dried till its weight becomes constant, then pheophorbide a is dissolved in acetone, strong inorganic base is added in the form of water solution of 0.05-1.00% concentration, stirred at 30-60° C. for 5-30 min, extra volume of strong inorganic base is added in the form of water solution of 1-50% concentration, the mixture is heated at 40-60° C. for 20-90 min, neutralised with diluted hydrochloric acid, chlorin $e_6$ precipitate is separated by centrifugation, washed with distilled water till acid reaction disappears, 55-80% of chlorin $e_6$ is obtained, then chlorin $e_6$ is recrystallised out of acetone in order to separate linear tetrapyrroles, chlorin $e_6$ is filtered out and washed with distilled water, chlorin $e_6$ is heated in sealed reservoir at the temperatures of 40-100° C. for 1 hour-30 days, then it is cooled and strong base solution is added till pH 7.5-8.5, then the solution is adjusted with apyrogenic water for injections to make photosensitizer concentration 6.5-7.5% $_{mass}$.

Furthermore, in the method of producing PS after the stage of addition of strong base till pH 7.5-8.5 the mixture may be gel filtrated to make chlorin $e_6$ percentage up to 80-90%, purpurin 5-up to 5-20% and purpurin 18-the rest, then diluted hydrochloric acid solution is added till photosensitizer precipitates, the solution is adjusted with apyrogenic water for

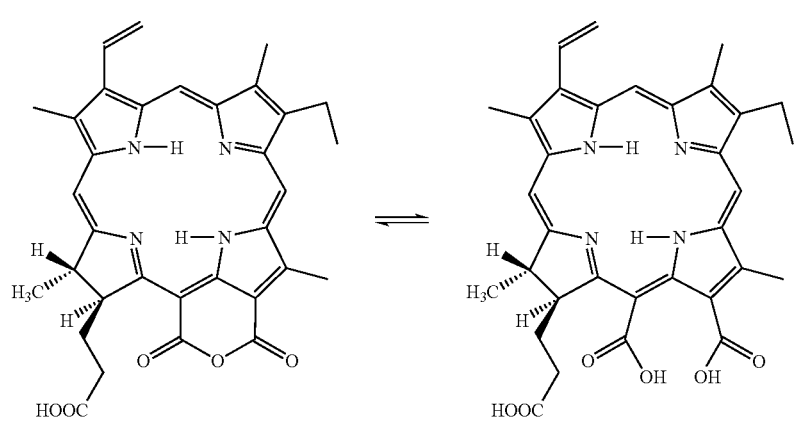

(III)

injections to make photosensitizer concentration 6.5-7.5% $_{mass}$, so the "Liquid extract of chlorins" is obtained.

Moreover, in the method of producing PS after the stage of gel filtration diluted hydrochloric acid solution may be added to the photosensitizer solution till photosensitizer precipitates, then the precipitate is filtered out or separated by centrifugation, the additives approved by RF State Pharmacopeia are added till pH 7.5-8.5, apyrogenic water for injections is added to make photosensitizer concentration 0.1-1% $_{mass}$, then bacteria are filtered out.

Also in the method of producing PS after the stage of gel filtration diluted hydrochloric acid solution may be added to the mixture till photosensitizer precipitates, this precipitate is filtered out or separated by centrifugation, adjusted with apyrogenic water for injections to make photosensitizer concentration 6.5-7.5% $_{mass}$, the "Liquid extract of chlorins" is dispersed in gel substrate according to he following ratio: 0.5-12% $_{mass}$ of the "Liquid extract of chlorins", 5-20% $_{mass}$ of dimethylsulfoxide, the rest is water, the additives approved by RF State Pharmacopeia and gel substrate.

Furthermore, in the method of producing PS after the stage of gel filtration diluted hydrochloric acid solution may be added to the mixture till photosensitizer precipitates, this precipitate is filtered out or separated by centrifugation, adjusted with apyrogenic water for injections to make photosensitizer concentration 6.5-7.5% $_{mass}$, and the resulting "Liquid extract of chlorins" is dissolved in dimethylsulfoxide according to the following ratio: 0.5-12% $_{mass}$ of the "Liquid extract of chlorins" and the rest is dimethylsulfoxide.

This method is realised with the use of standard laboratory chemical pilot equipment: biomass is treated in 10-50 L aluminium vessels equipped with mechanical stirrer, biomass is filtered through 5-20 L nutch filters with oil vacuum pump and liquid nitrogen-cooled trap, biomass is centrifuged in the cooled floor centrifuge with 4×1 L buckets and rotation speed of 6000 rpm, extract is acidified in glass 20 L bottles, precipitated pheophytin a is filtered through 5-10 L nutch filters with oil vacuum pump and liquid nitrogen-cooled trap, pheophytin a is hydrolysed in 0.1-0.5 L heated three-neck round-bottom flasks equipped with stirrer, backflow condenser and feeding hole with stopper, solutions are washed in 2 L separating funnels, neutralised in 2-5 L chemical beakers, pheophorbide a is filtered through 2-5 L nutch filters with oil vacuum pump and liquid nitrogen-cooled trap, recrystallised in 0.25-1 L chemical flat-bottom flasks, pheophorbide a is dissolved in acetone and reacted with strong inorganic base in 0.5-2 L heated three-neck round-bottom flasks equipped with stirrer, backflow condenser and feeding hole with stopper, chlorin $e_6$ precipitate is separated in the cooled floor centrifuge with 4×0.5 L buckets and rotation speed of 6000 rpm, chlorin $e_6$ is recrystallised in 0.25-0.5 L, 2-5 L chemical flat-bottom flasks, chlorin $e_6$ is filtered through 1-2 L nutch filters with oil vacuum pump and liquid nitrogen-cooled trap, chlorin $e_6$ is heated in 0.05-0.1 L round-bottom chemical flasks of heat-resistant glass, it is reacted with strong base solution and adjusted in 0.1-1 L chemical beakers with the use of standard pH-meter and spectrophotometer, mixture is gel filtrated on a column of 50-10 mm diameter and 100-150 mm height, bacteria are filtered out through standard 0.22 μm microporous filter of Millipore type, the "Liquid extract of chlorins" is dispersed in gel substrate with the use of cutter or bead homogenizer, moreover, 0.01-10 L cone flasks with stoppers, 0.005-2 L cylinders, 0.05-2 L beakers, 20 L bottles, weigher with 1-1000 g range and magnetic stirrers are used for preparing samples and solutions; 5 L round-bottom flasks with thermometer and direct-flow water condenser are used for acetone and hexane regeneration; rotary vacuum evaporator is used for quick removing of solvents at low temperature.

According to the method of producing PS the concentrated hydrochloric acid solution is considered as saturated hydrogen chloride water solution at the temperature of 20° C. that commonly contains 36-37% $_{mass}$ of hydrogen chloride.

At the stage of pheophytin a turning into pheophorbide a the range of hexane and acetone volumes (6-16 ml of acetone and 0.6-6 ml of hexane) is explained by the fact that if lesser volumes of solvents are used pheophytin a dissolving is not complete and if the volumes are greater the solution would not be enough concentrated for fast hydrolysis. The range of hydrochloric acid volumes (5-10 ml) is explained by the fact that if the volume is lesser the pheophorbide a yield decreases and if the volume is greater the reaction selectivity decreases due to formation of by-product pyropheophorbide a. The temperature range of 40-60° C. is explained y the fact that if the temperature is lower the pheophorbide a yield decreases and if the temperature is higher the reaction selectivity decreases due to formation of by-product pyropheophorbide a. The time range of 20 min-1 hour is explained by the fact that if this period is shorter the pheophorbide a yield decreases and if this period is longer the reaction selectivity decreases due to formation of by-product pyropheophorbide a. The volume of hexane added (6-16 ml) is explained by the fact that if this volume is lesser the separation of one of the reaction products, phytol, from the reaction mixture is not effective, and the use of greater hexane volume is not rational.

At the stage of pheophorbide a purification organic phase is washed with the mixture of acetone and concentrated hydrochloric acid in the ratio of 2:1 to 10:1. If this ratio is lesser than 2:1 the flaky admixture precipitate is formed that is hard to separate from the water phase containing the target pheophorbide a. If this ratio is greater than 10:1 the water phase becomes oversaturated with acetone and the admixtures come into it from the hexane phase, contaminating the target pheophorbide a.

At the stage of pheophytin a turning into chlorin $e_6$ the strong base concentration lays in the range of 0.05-1.00%, its lower limit being the minimum that is necessary for the reaction of pheophorbide a cyclopentanone ring (E ring) opening, and if he base concentration is greater than 1% the E ring allomerisation (oxidation) reaction takes place leading to "unstable chlorin" instead of the target chlorin $e_6$, and then leading to purpurin 18, and further—to chlorin $p_6$.

Then, according to the method, an extra volume of strong inorganic base is added in the form of water solution of 1-50% concentration. If this concentration is less than 1% incomplete saponification of ester group at the $13^{th}$ or $15^{th}$ position takes place. If the base concentration is greater than 50% tetrapyrrole macrocycle of PS opens in some cases.

Then the reaction mass is stirred at 30-60° C. for 5-30 min, the lesser temperature facilitating the E ring allomerisation process, and the higher temperature facilitating chlorin $e_6$ decomposing to chlorin $e_4$. When adding an extra amount of strong inorganic base the temperature range is 40-60° C. and the time range is 20-90 min. If time and temperature are less than stated the methyl ester at the $15^2$ position has no time to hydrolyze, if time and temperature are greater by-product chlorin $e_4$ yield increases.

When chlorin $e_6$ turning into the "Liquid extract of chlorins" the process of oxidation and the subsequent thermolytic processes of dehydration and decarboxylation of PS with oxidized methylene group in the $15^1$ position into purpurin 5 take place:

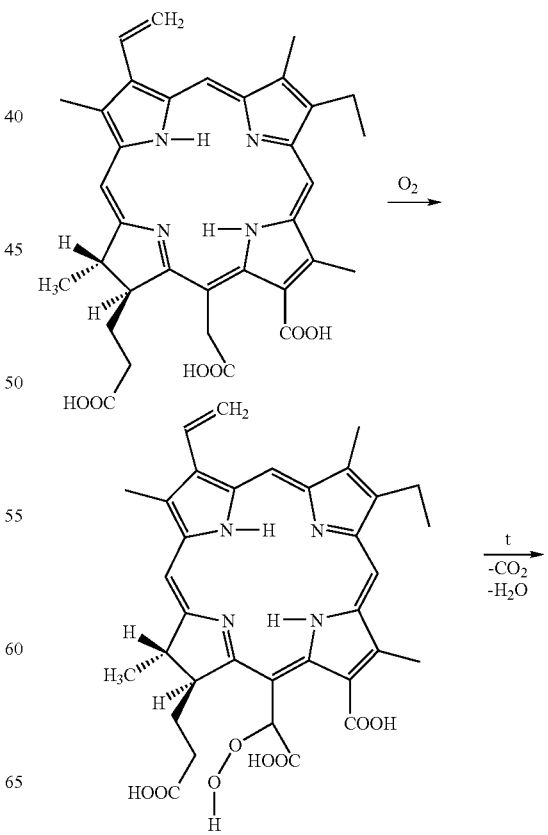

-continued

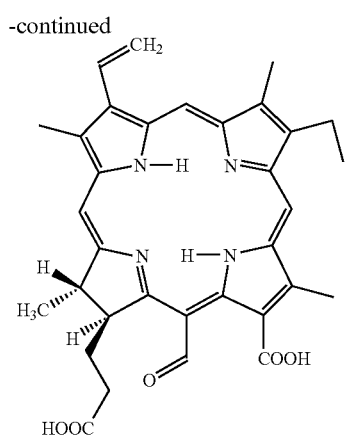

When chlorin $e_6$ turning into the "Liquid extract of chlorins" the use of the temperature less than 40° C. requires long reaction time, this being technologically irrational. The use of the temperature higher than 100° C. results in the acceleration of substance decomposing.

Duration of the process less than for 1 hour requires the use of temperatures above 100° C., or results in the substance having a low biological activity.

Duration of the process greater than for 30 days is accompanied by irreversible change (decomposing) of substance.

The optimal process temperature is 45-70° C. (FIG. 1).

The optimal process duration is 2-9 days at 70° C. (FIG. 2) or 1-48 hours at 100° C. (FIG. 3), resulting in 5-20% of purpurin 5 in an admixture.

The substance containing 5-20% of purpurin 5 and 80-95% of chlorin $e_6$ in composition of active agent (PS) is suitable for producing water-soluble injection medicinal forms. If the substance contains less than 5% of purpurin 5 it has a low biological activity. If the substance contains more than 20% of purpurin 5 its water solubility worsens, that unfavorably affects the stability of medicinal forms at storage and worsens the ability to filtration through microporous filters. The last property is necessary for sterilisation of medicinal forms as tetrapyrroles medicinal forms cannot be sterilised by heating or UV irradiation because of high probability of undesirable chemical changes.

80-95% chlorin $e_6$ contents in the substance is necessary for keeping purpurin 5 in water-soluble state.

The pH interval results from the fact that its lower value—pH 7.5—is the lower limit of chlorins solubility in water solutions resulting in concentrations suitable for pharmaceutical utilisation, without adding solubilizers. The upper limit—pH 8.5—is the limit of biological tolerance of hydroxide ions, [OH⁻].

The interval of chlorin $e_6$ concentrations 6,5-7,5% results from the use of technological methods of centrifugation or filtration at the stage of separating chlorin $e_6$ precipitate, these methods giving the product within this range of concentrations.

The invention is illustrated by drawings, on which

FIG. 1 relates to the method and shows formation of purpurin 5 depending on temperature at incubation for 30 days FIG. 2 shows the dependence purpurin 5 content on incubation time at the temperature 70° C.;

Figure 5A:
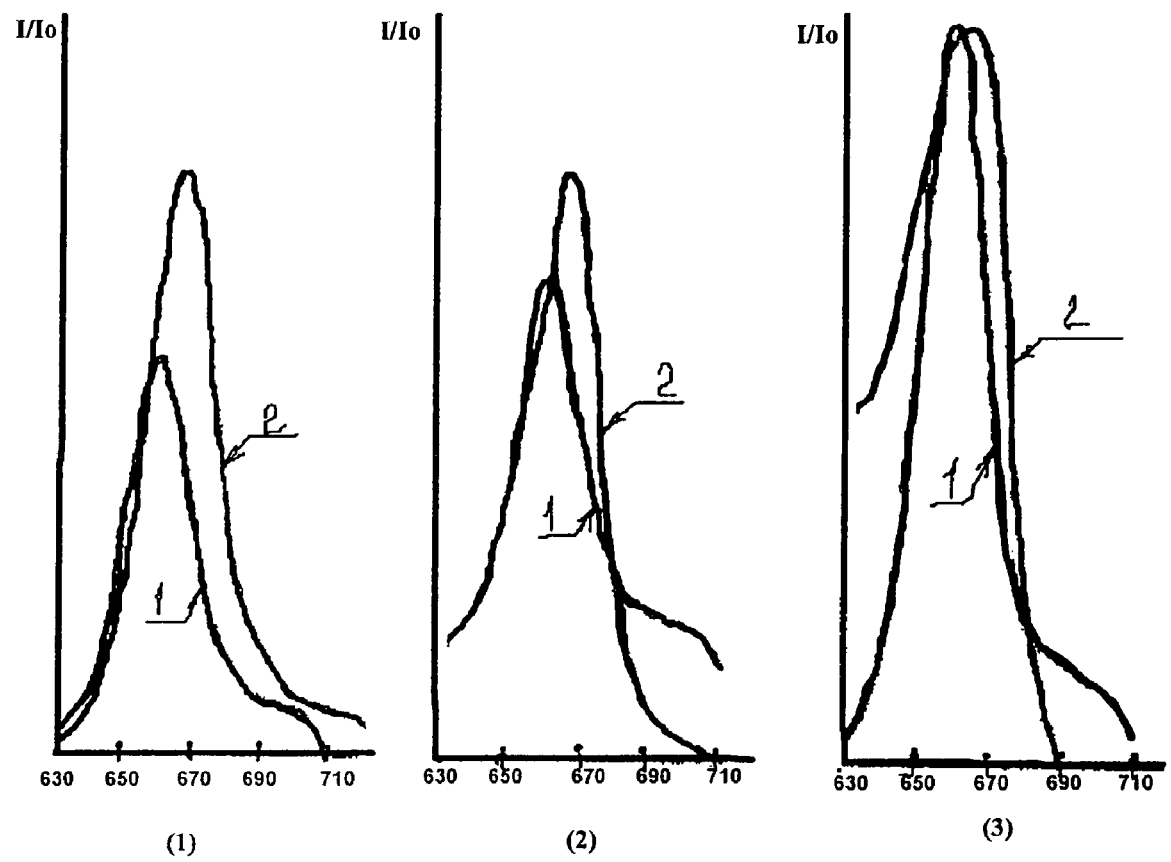
FIG. 5a shows the presence of a chlorin $e_6$ metabolite (formula I), namely purpurin 5 (formula II), in blood, and the curves marked as "1", are taken for PS in 0,01 M borate buffer with pH 9.18, and the curves marked as "2", are taken for PS in blood.
Figure 5B:
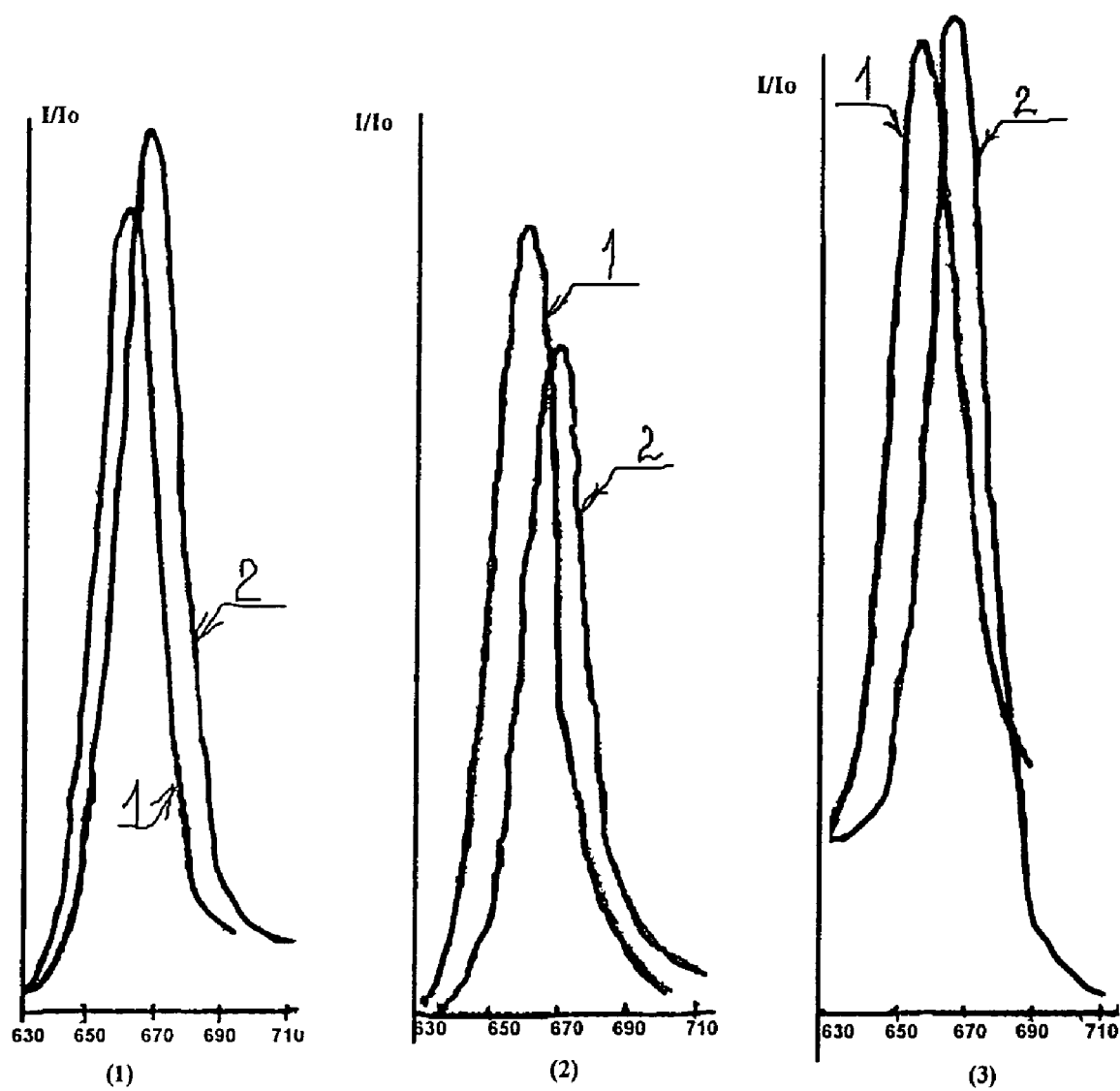
Figure 6:
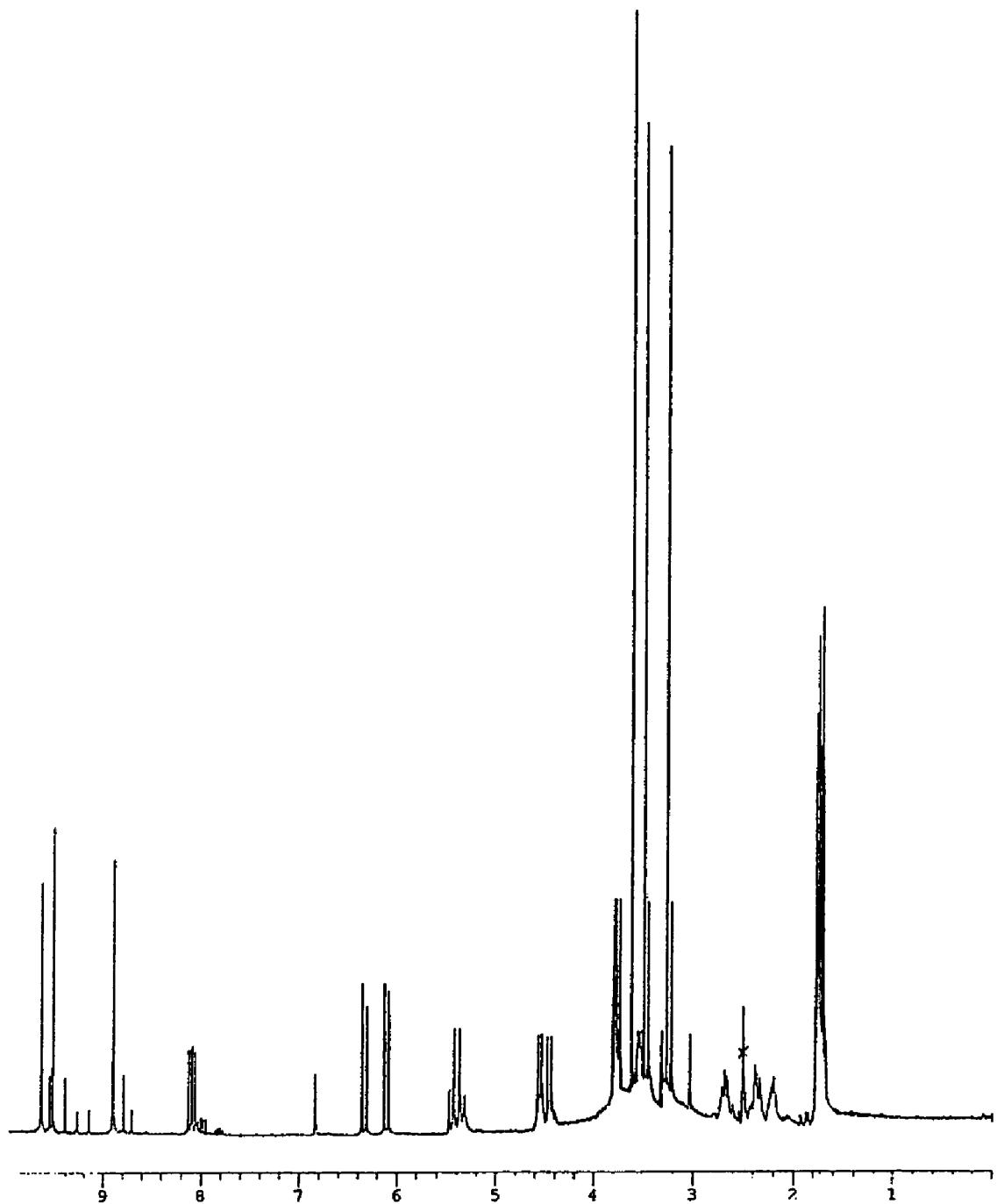
Figure 7:
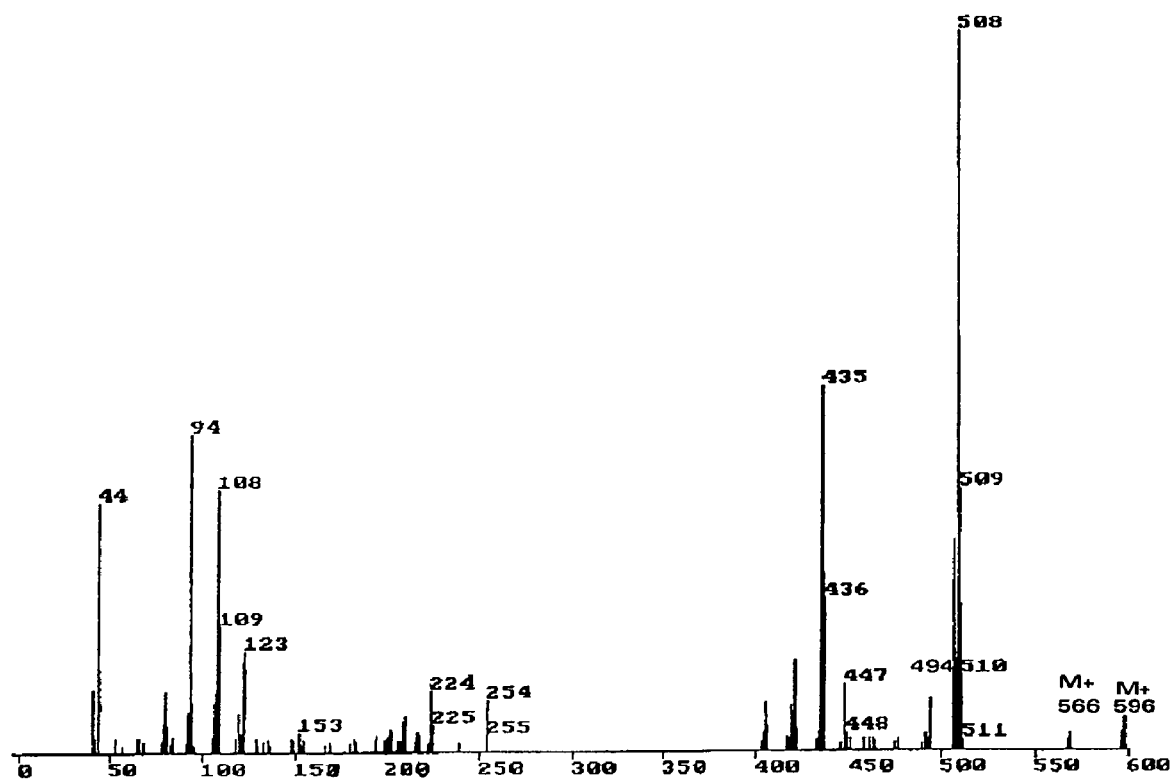
Figure 8:
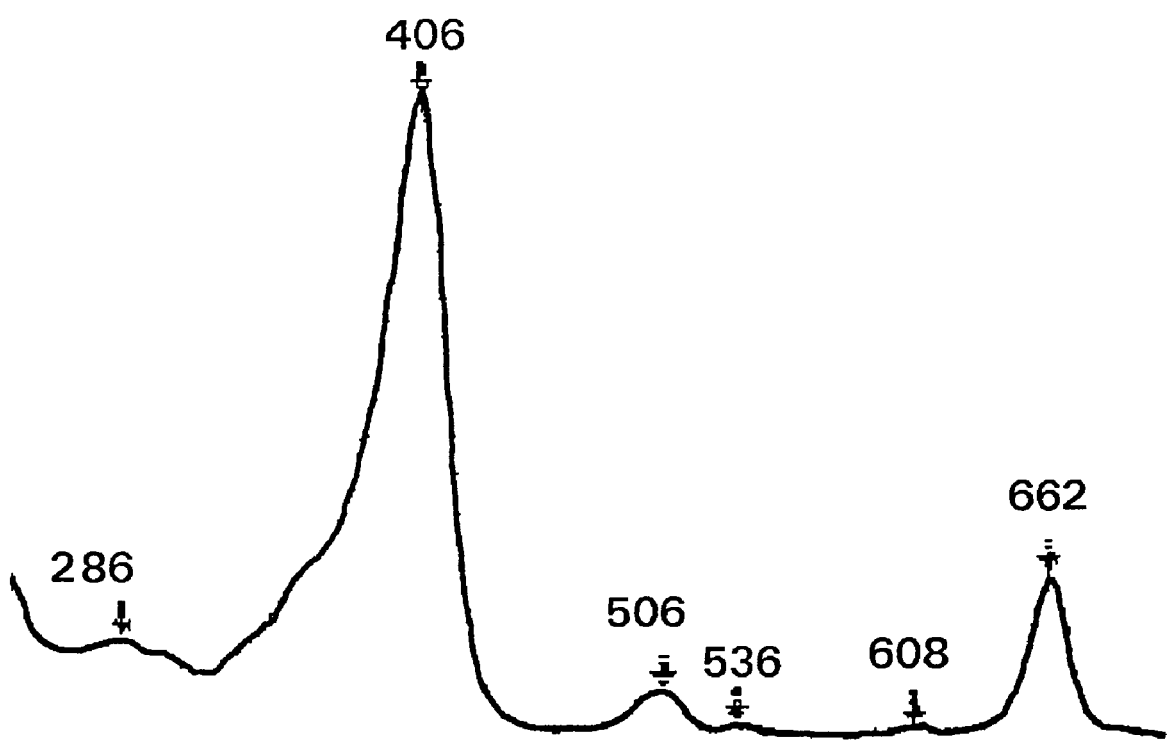
Figure 9:
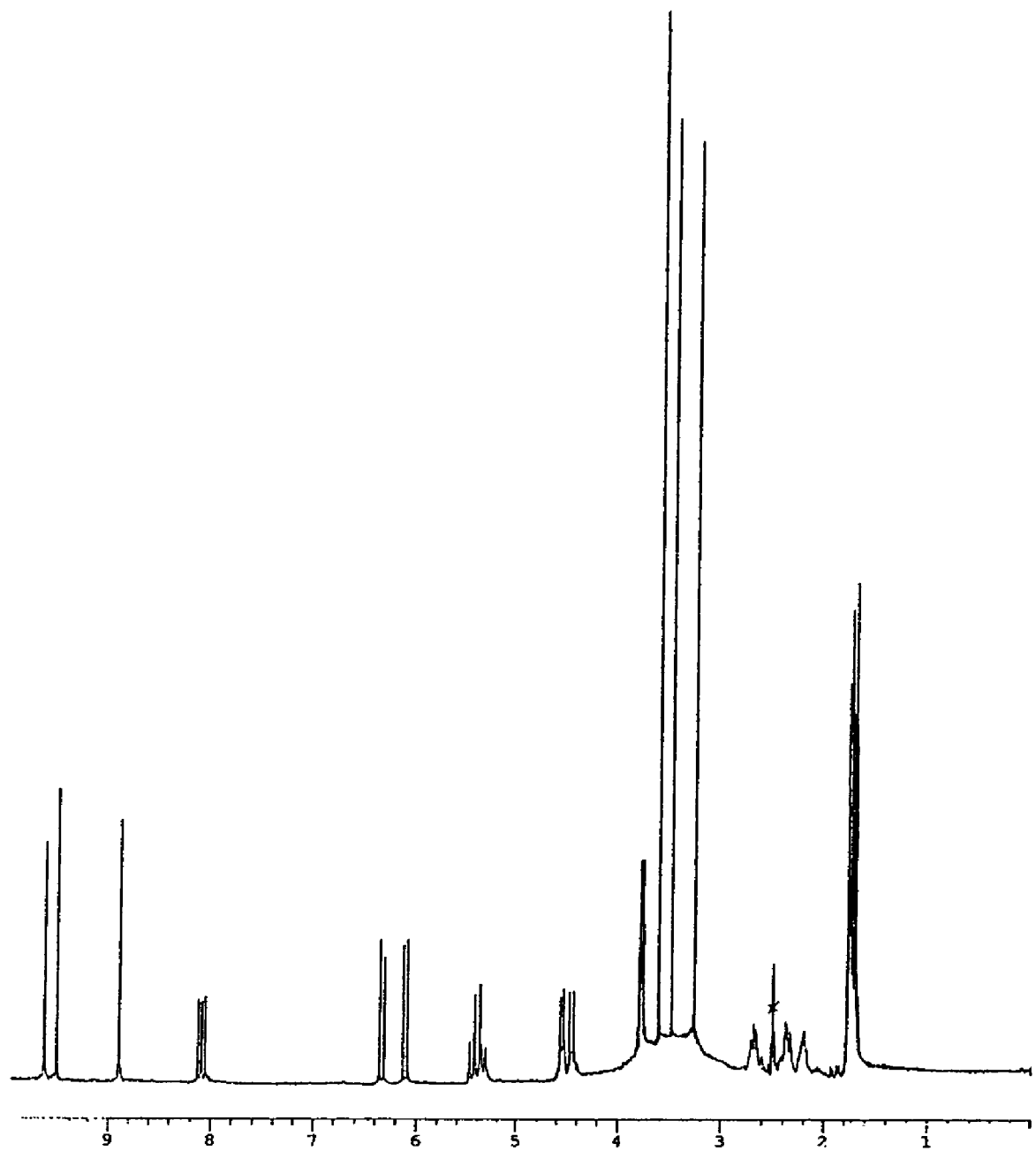
Figure 10:
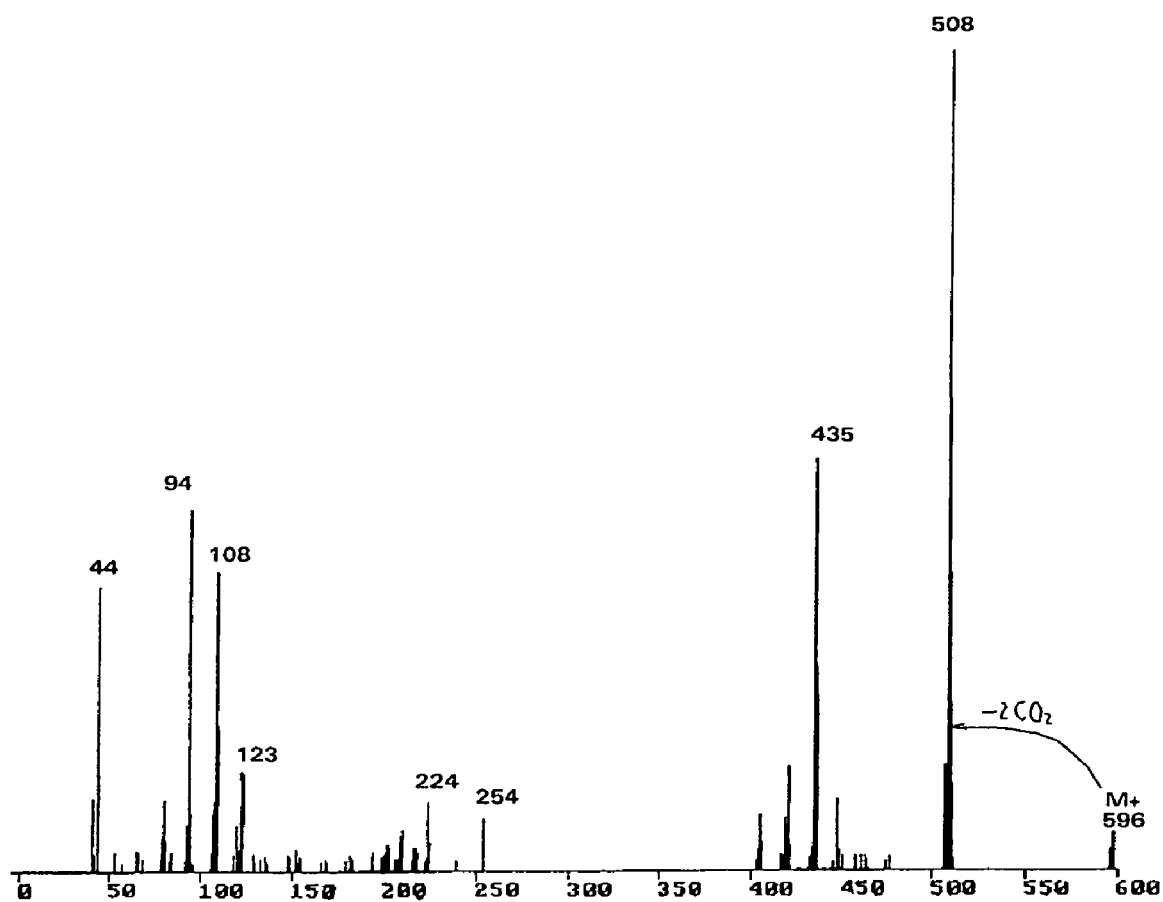
Figure 11:
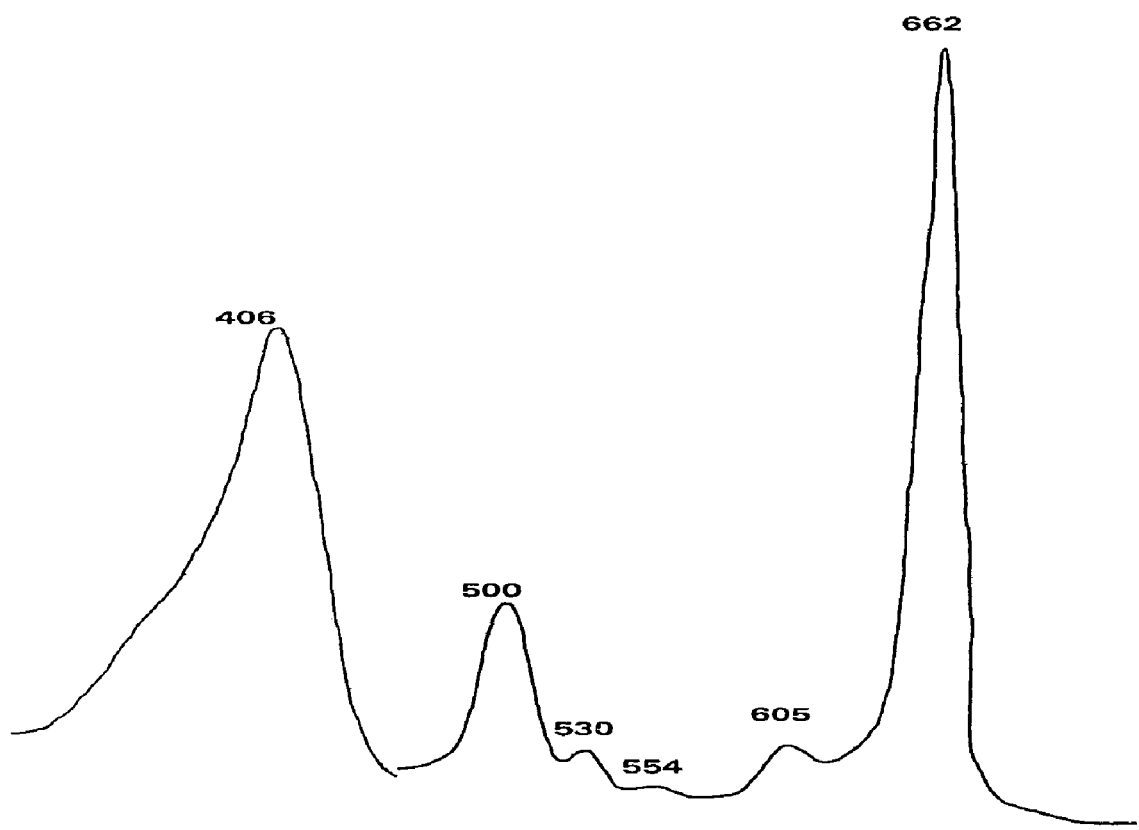
Figure 12:
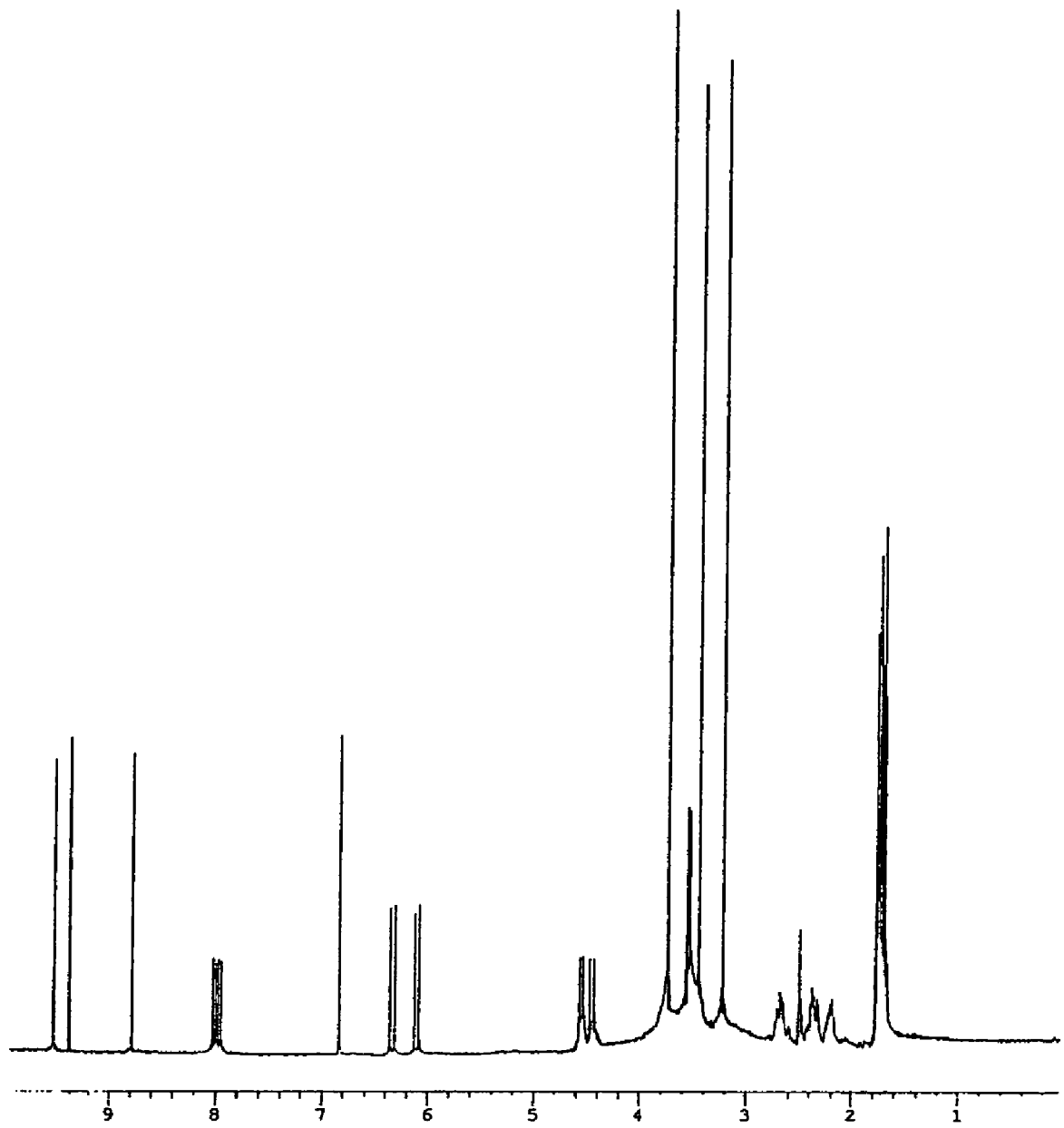
Figure 13:
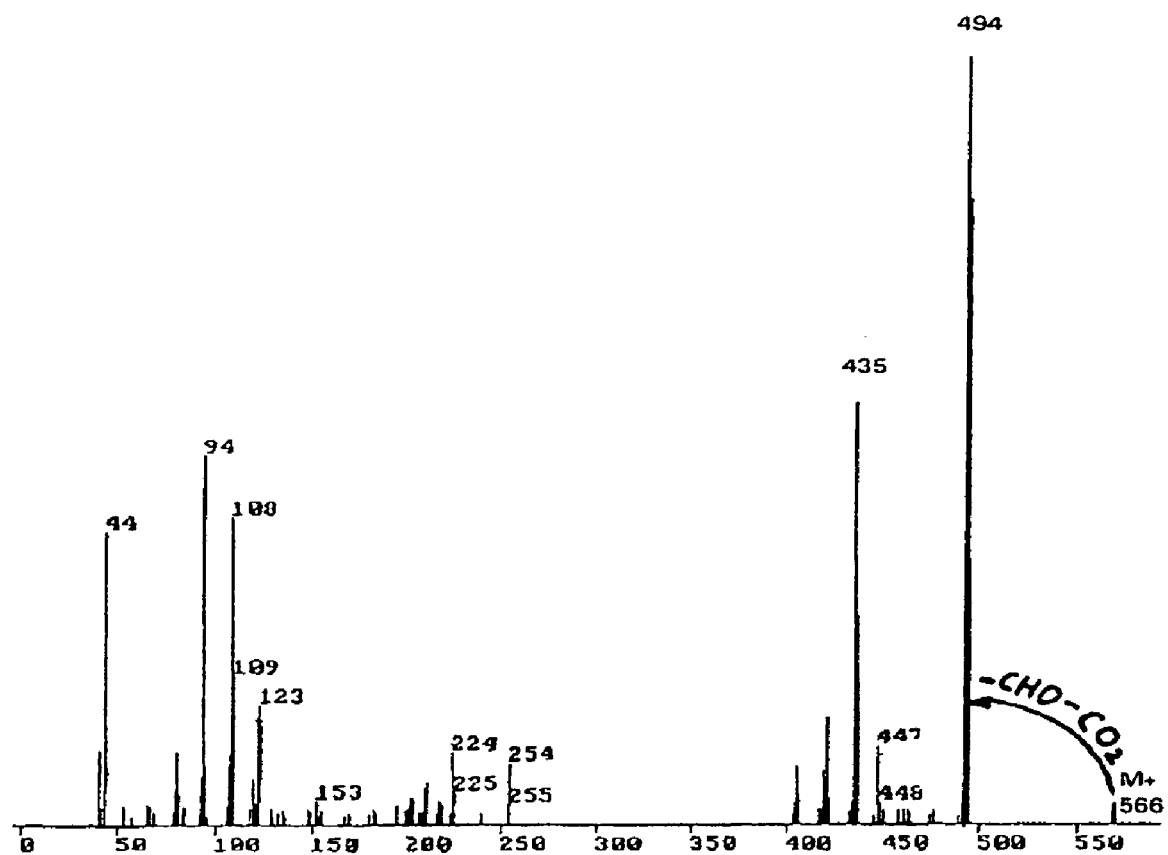
Figure 14:
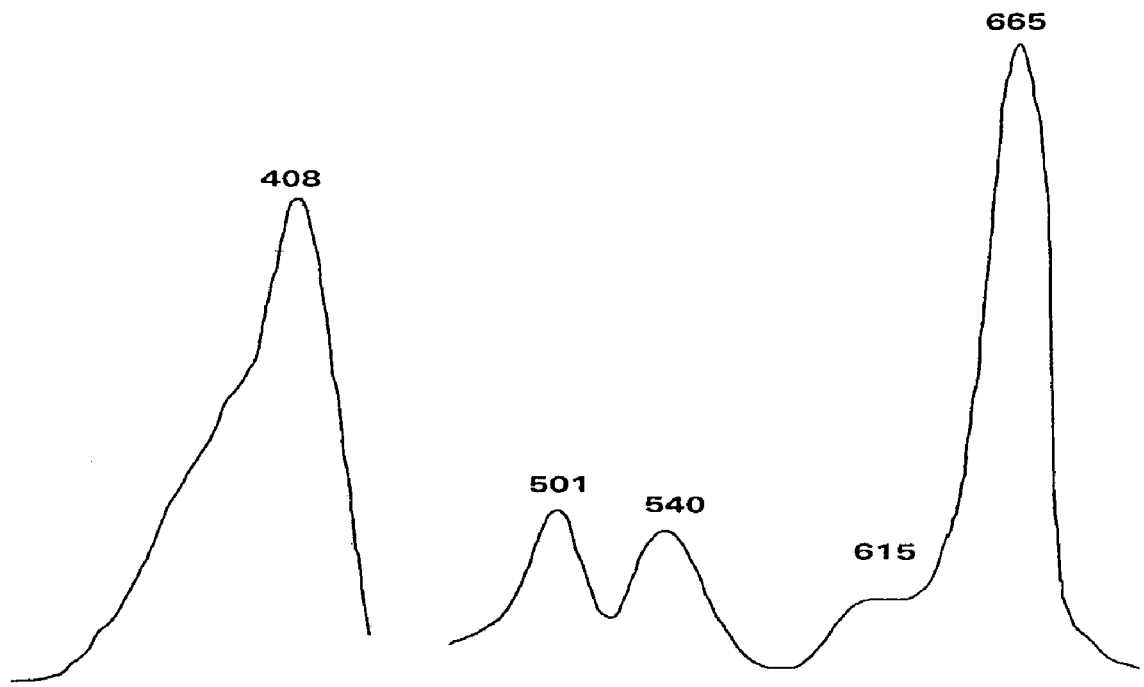
Figure 15:
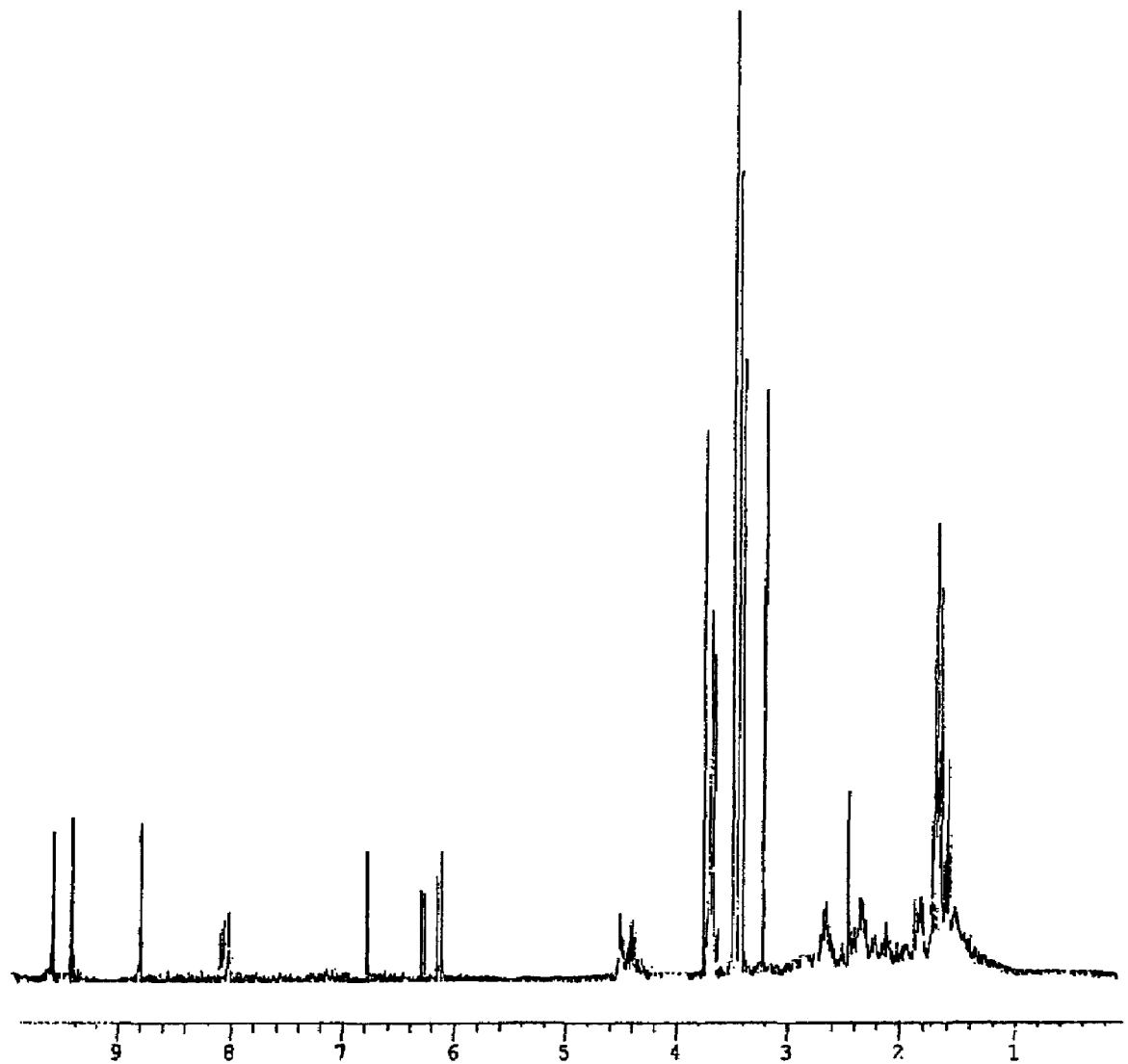
Figure 16:
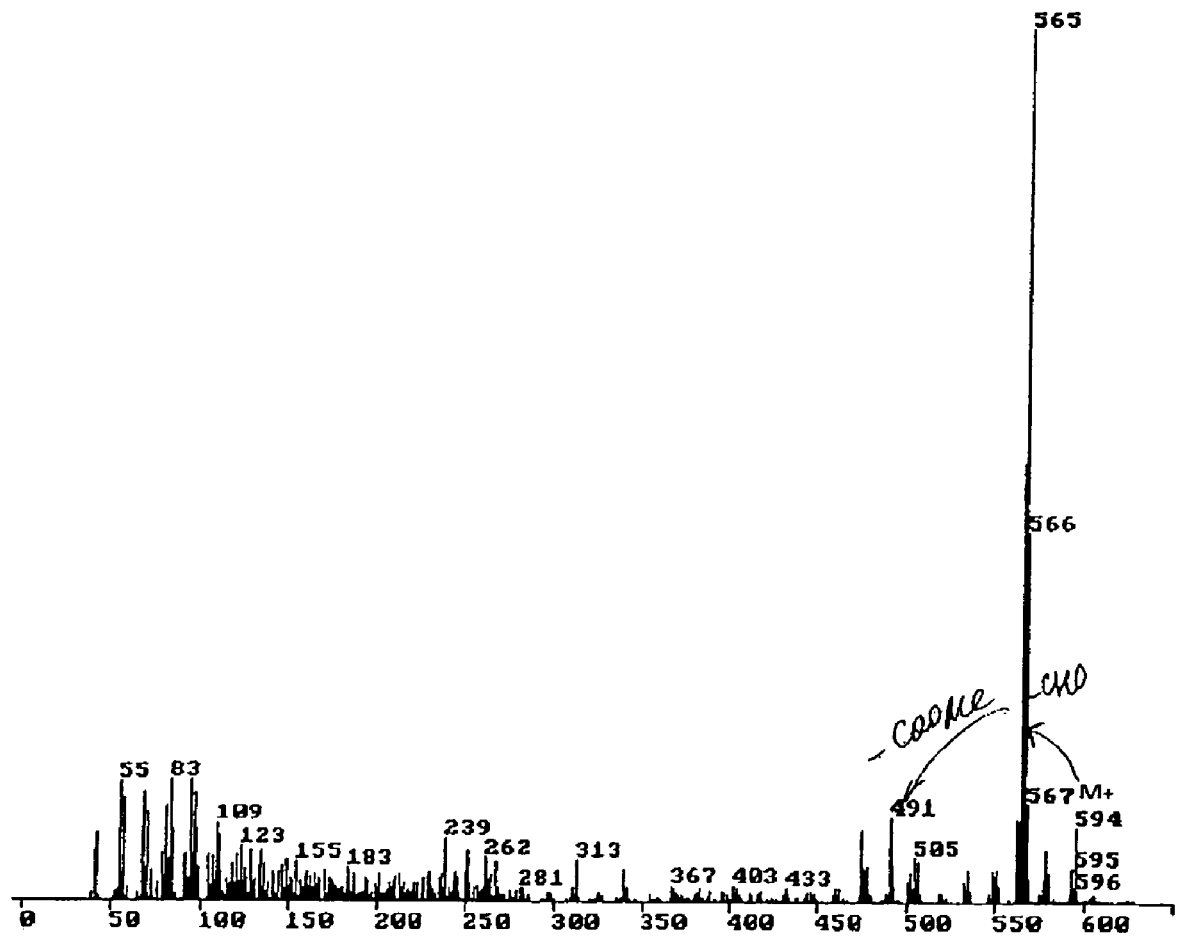
Figure 17:
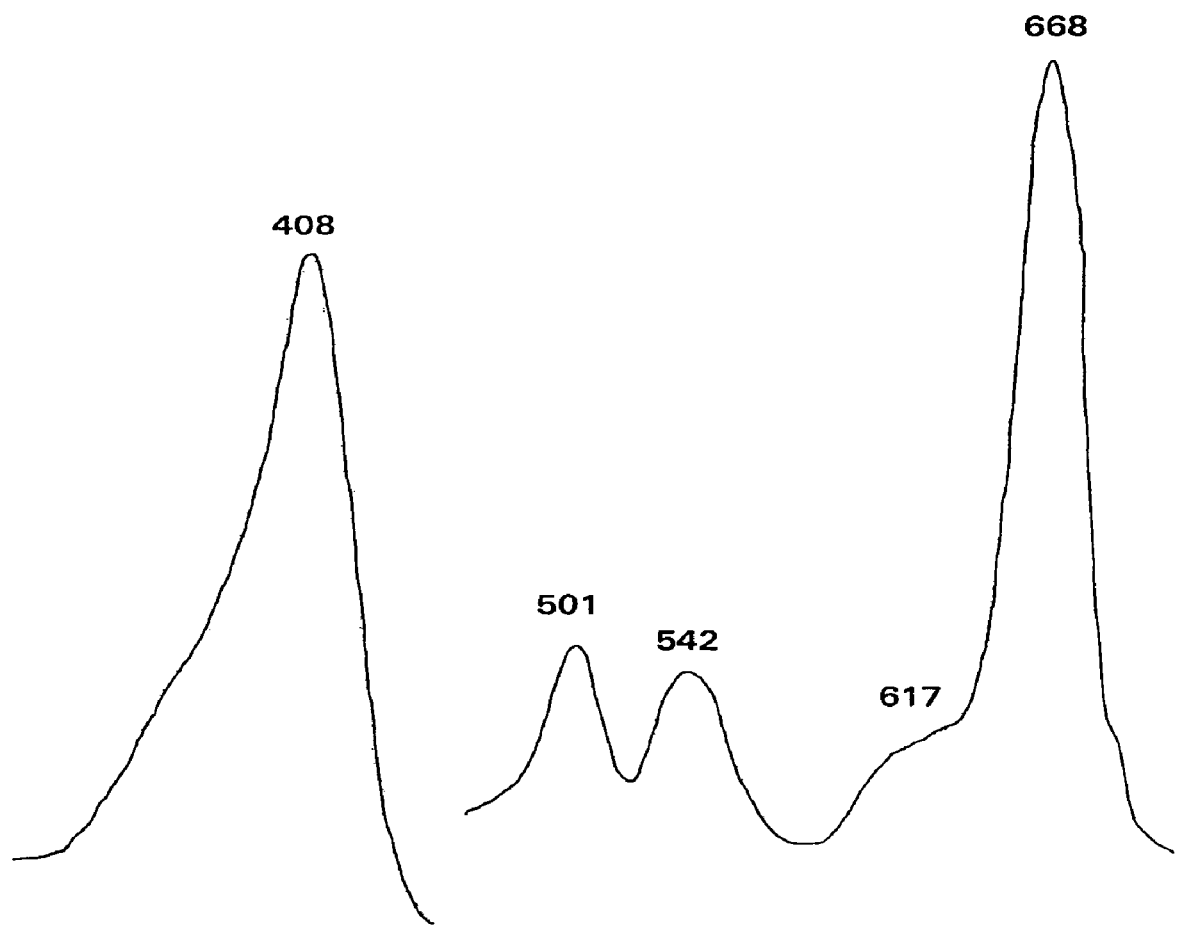

FIG. 5b confirms the chlorin $e_6$ metabolism (formula I) into purpurin 5 (formula II) in liver;

FIG. 6 shows the PMR spectrum of "Liquid extract of chlorins" substance, obtained in Example 2;

FIG. 7 shows the mass spectrum of "Liquid extract of chlorins" substance, obtained in Example 2;

FIG. 8 shows the absorption visible spectrum of "Liquid extract of chlorins" substance, obtained in Example 2, the spectrum is taken in ethanol, substance concentration is 5 mkg/ml;

FIG. 9 shows the PMR spectrum of chlorin $e_6$;

FIG. 10 shows the mass spectrum of chlorin $e_6$;

FIG. 11 shows the absorption visible spectrum of chlorin $e_6$, the spectrum is taken in ethanol, chlorin $e_6$ concentration is 15 mkg/ml (Sore band-5 mkg/ml);

FIG. 12 shows the PMR spectrum of purpurin 5;

FIG. 13 shows the mass spectrum of purpurin 5;

FIG. 14 shows the absorption visible spectrum of purpurin 5, the spectrum is taken in ethanol, purpurin 5 concentration is 15 mkg/ml (Sore band-5 mkg/ml);

FIG. 15 shows the PMR spectrum of purpurin 5 dimethyl ester;

FIG. 16 shows the mass spectrum of purpurin 5 dimethyl ester;

FIG. 17 shows the absorption visible spectrum of purpurin 5 dimethyl ester, the spectrum is taken in ethanol, purpurin 5 DME is 15 mkg/ml (Sore band-5 mkg/ml).

PS is illustrated by Example 1, examples of method realisation are given in Examples 2, 3, special cases of method realisation are illustrated in Examples 4-9.

In respect to chemistry PS comprises three cyclic tetrapyrroles of the chlorin nature (with hydrogenated D ring)—chlorin $e_6$ (Formula I), purpurin 5 (Formula II, Example 10) and purpurin 18, which gradually turns into chlorin $p_6$ in alkaline medium (at storage) (Formula III).

In respect to physical chemistry PS possesses the ability to absorb light in visible spectrum, resulting in PS photoactivation and the subsequent relaxation of excited state with transfer of energy to molecular oxygen and organic substrates dissolved in tissues. This transfer leads to oxidising and free-radical processes in biological tissues and their damage and the subsequent destruction (necrosis). The most preferable excitation band for PDT is the long-wavelength band (Tab. 1) since penetrating power of light in biological tissues increases along with increase in wavelength. Thus, PS is capable to damage biological objects on depth up to 10 mm after excitation by light with wavelength 654-670 nm.

In respect to pharmaceutics PS is "Liquid extract of chlorins" substance (extracts are considered as liquid if the effective agent concentration is less than 20%). The given substance is considered as extract due to the necessity of its extraction from a biomass with the use of organic solvents.

TABLE 1

Absorption maximum positions and molecular extinction of absorption values for a long-wave band of "Liquid extract of chlorins" in different media.

| PS | $\lambda_{max}$, nm<br>$\epsilon$, M⁻¹cm⁻¹<br>(0.01 M borate buffer,<br>pH 9.18) | $\lambda_{max}$, nm<br>$\epsilon$, M⁻¹cm⁻¹<br>(0.01 M borate buffer<br>with 1% human serum albumin, pH 7.2) | $\lambda_{max}$, nm<br>$\epsilon$, M⁻¹cm⁻¹<br>(ethanol) |
|---|---|---|---|
| "Liquid extract of chlorins" | 654.5 (28270) | 662 (34200) | 662 (34230) |

Compound of formula II possesses the ability to accumulate selectively in malignant neoplasms and infected focuses but it is weakly soluble in water, and compound of formula I, alongside with expressed photodynamic activity, is a solubilising agent for compound of formula II.

Figure 1:
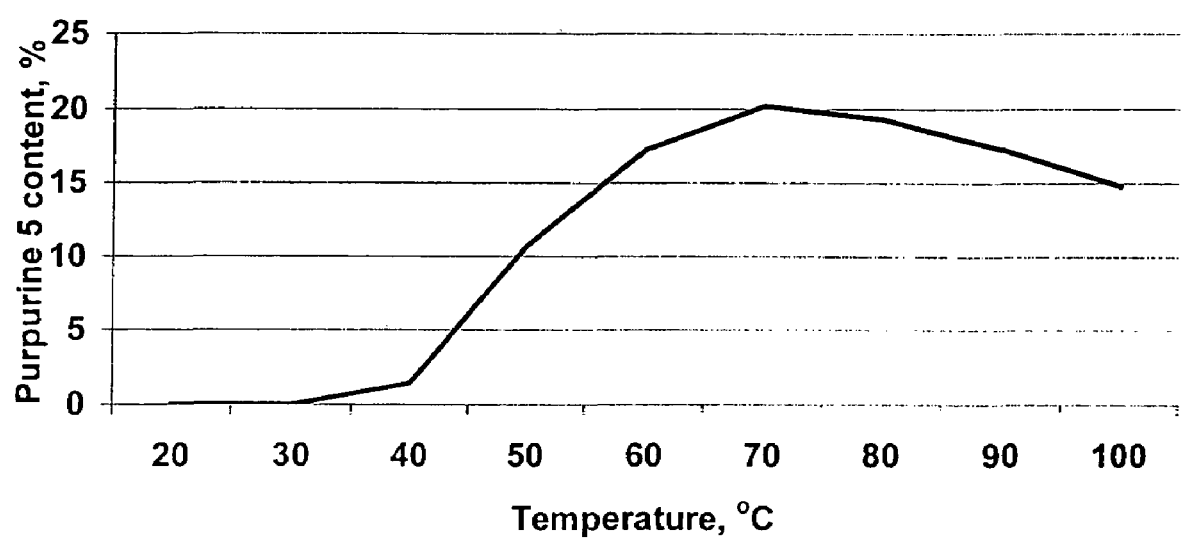
Figure 2:
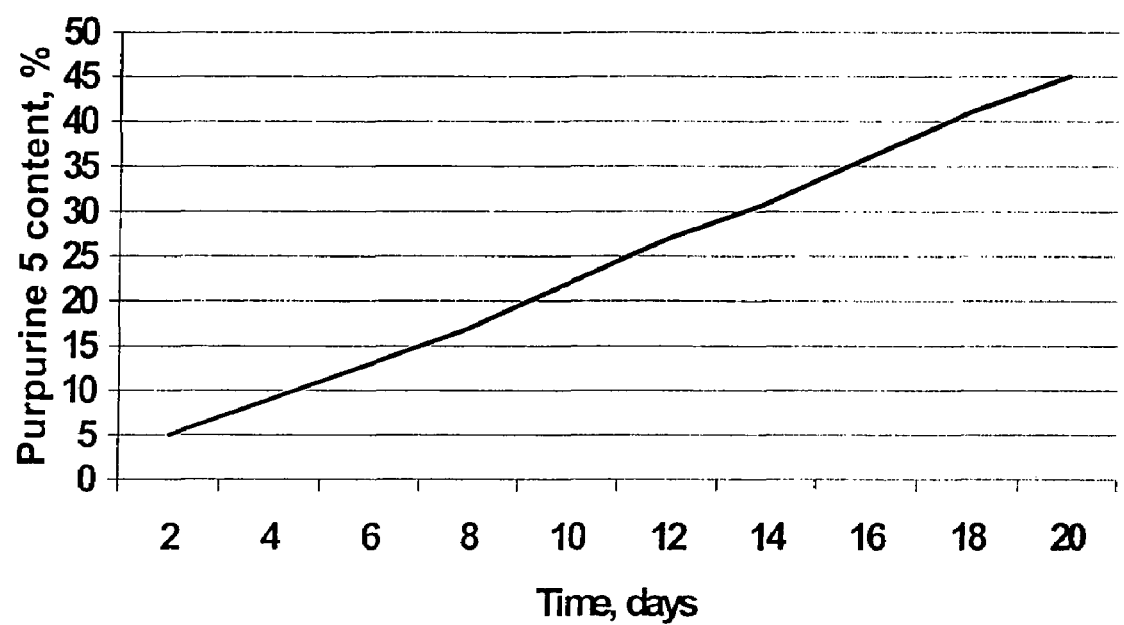
Figure 3:
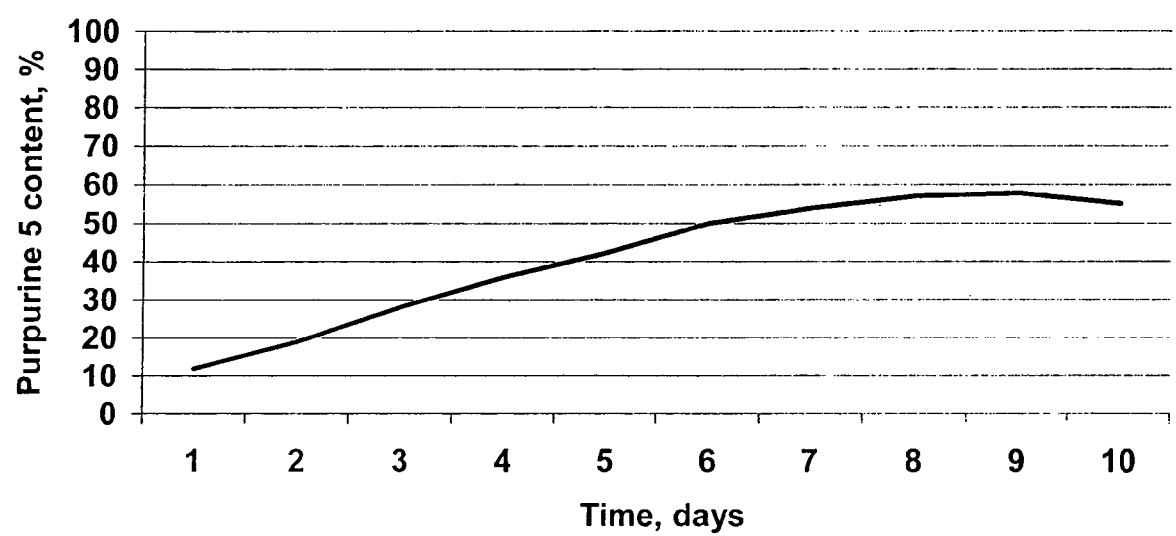
FIG. 3 shows the dependence of purpurin 5 content on incubation time at the temperature 100° C.
Figure 4:
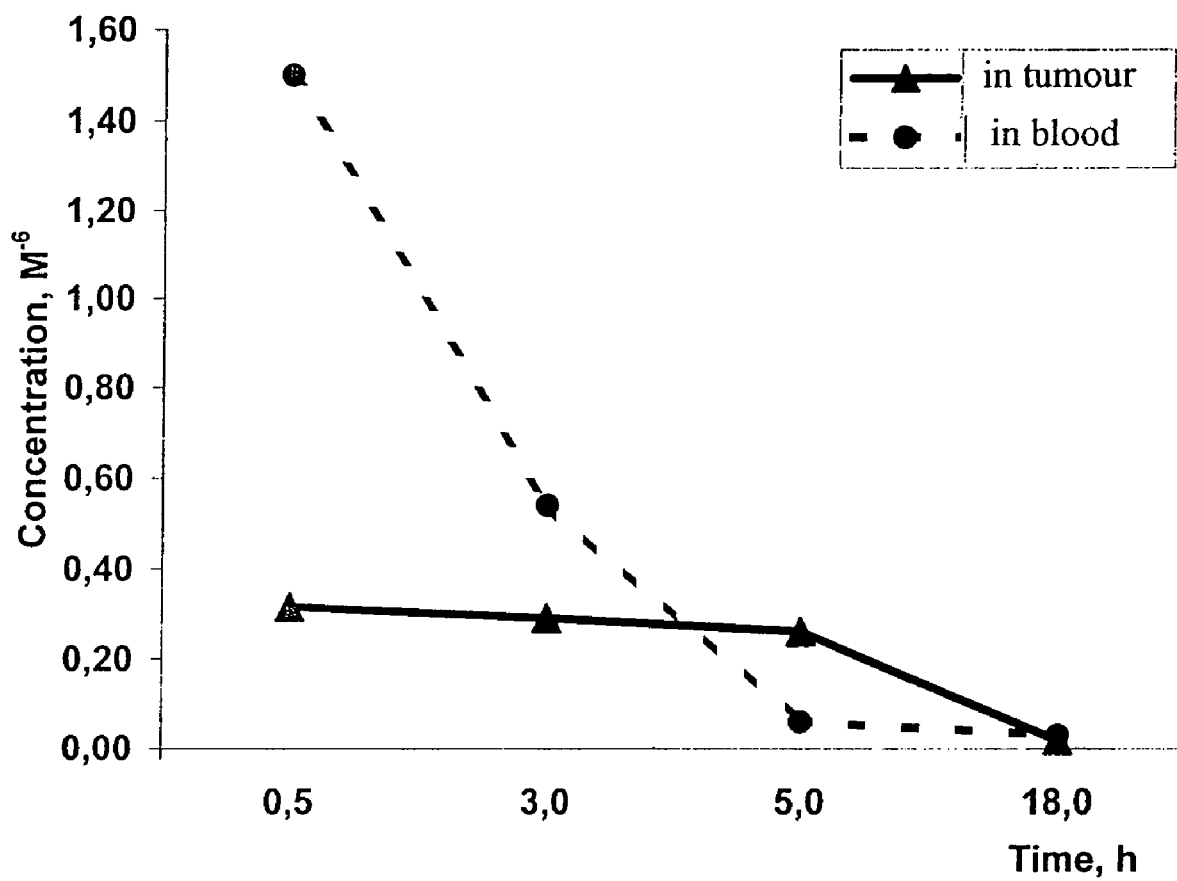
FIG. 4 illustrates the pharmacokinetics of "Liquid extract of chlorins" substance, used as the medicinal form "Radachlorin, 0.5% solution for injections" ("Photochlorin") at tumorous mice at intravenous introduction in the dose of 20 mg/kg.

With respect to pharmacology (FIG. 4, Example 11) the uniqueness of pharmacokinetic parameters is achieved by the fact that in an organism PS of formula (I) slowly turns into PS of formula (II), this process keeps the concentration of the last at a constant level from the moment of introduction into the organism till the moment of excretion out of a tumour, during a time interval sufficient for effective PDT realisation. After the suggested PS composition is introduced into the organism of tumorous mice it comes into a blood flow, and due to blood circulation mainly of the compound of formula I high and stable PS concentration—0.27-0.32 µM, sufficient for effective PDT in the interval of 0,5-4 hours, is achieved in the first 3 hours post introduction in the area of a tumour. Within this period high contrast is achieved due to the presence of 5-20% of the compound of formula (II) in a composition, this compound possesses the ability to accumulate in a tumour with high contrast, the maximum of accumulation falling on the moment of 3 hours post PS introduction into an organism of animals (the index of contrast is 14.5 for skin and 2.9 for muscles). Within this time the compound of formula (I) turns into the compound of formula (II) in the organism, providing high stable PS concentration in the area of a tumour in the interval of 3-5 hours after injection, this concentration gradually decreases, remaining therapeutically sufficient up to 18 hours after injection. Then the compound of formula (II) dissociates in the organism to nontoxic products that are excreted through a liver.

Chlorin $e_6$ of formula (I) transformation into purpurin 5 of formula (II) is proved by fluorescence spectra of experimental animals' organs and tissues samples (FIG. 5). When adding the "Radachlorin, 0.5% solution for injections" ("Photochlorin") medicinal form to blood homogenate in the concentration of 10 µM with the subsequent spectrophotometric analysis the change of fluorescence spectrum in the form of 1.2 times widening and fluorescence intensity maximum shift to a long-wave spectral region by 8 nm is observed. When adding "Photochlorin" in a smaller concentration (C=1 µM) only the shift of a spectrum without widening is observed, that shows the dose effect at metabolite formation.

FIG. 5a, (3) shows the result of blood homogenate analysis, received 3 hours after "Photochlorin" introduction into mice. The most expressed parameter here is 1.5 times widening of a spectrum at the maximum shift of a band to a long-wave spectral region by 4 nm, this indicating that a mixture of "Photochlorin" and metabolite is present in the analysed blood sample.

When adding "Photochlorin" in concentration of 10 µM to a test tube with liver homogenate [FIG. 5b, (1)] the change of spectral characteristics is expressed first of all in shift of fluorescence intensity maximum to a long-wave spectral region by 9 nm. The widening of a spectrum is not observed.

The similar picture is observed when adding "Photochlorin" in smaller concentration C=1 µM [FIG. 5b, (2)].

When liver tissue homogenate obtained 3 hours after the preparation introduction into animals is analysed the spectrophotometric picture of a sample is similar to two previous [FIG. 5b, (3)].

Thus, the received data show the "Photochlorin" metabolite presence in liver homogenates.

The purpurin 5 accumulation in tumours of experimental animals, optimal for photodynamic effect according to selectivity, is observed within the time interval of 3-18 hours after intravenous or intraperitoneal introduction. In cases when it is necessary to enable also the chlorins substance circulating in a blood flow, the irradiation optimum time is 0,5-4 hours after intravenous introduction. Generally, for realising PDT with "Liquid extract of chlorins", the interval between introduction of a preparation and irradiation makes 0,5-18 hours.

Biological activity of the medicinal form "Radachlorin, 0.5% solution for injections" ("Photochlorin"), containing 0.5% of anhydrous "Liquid extract of chlorins" substance, is estimated in vitro and in vivo.

PS balance according to amphiphilicity is proved by standard experiment in vitro (Kessel D. Biochemistry. 1977. V. 16. p. 3443-3449) (Tab. 2, Example 12). PS distribution coefficient in 1-octanol/phosphate buffer, pH 7.4 (Cd) is 1.40. It means that the claimed PS is equally well soluble both in aqueous and in lipidic phase and it proves PS lipophily which allows this compound to be redistributed from water into complexes with transport proteins and lipoproteins, to penetrate rapidly into cells and to accumulate in cytoplasmic intracellular membranes and microsomes, or to penetrate into cells by diffusion through a plasmatic membrane of these cells. After laser irradiation the compound deposited in such a way evolves singlet oxygen inside a cell and kills it.

PS antitumor activity towards different types of cancer cells is proved by the results obtained in in vitro experiment in which 3 lines of cultured tumor cells: rat pheochromocytomes PC12, rat Gasser's ganglion neurinoma RGGN1 and rat hepatoma 27 (Hep27), were used (Tab. 2, Example 13).

The following methods are used for study of dose-dependent cytophototoxic (after laser irradiation) and biological "dark" activity of PS:

1. MTT-test that allows to define precisely the number of living cells after their PS treatment and laser irradiation in order to calculate cytotoxic and cytophototoxic indexes of PS. The same test allows to estimate dose-dependent cytotoxic and biological "dark" activity of PS (Andrei V. Reshetnickov, Gelii V. Ponomarev, Andrei V. Ivanov, Olga Yu. Abakumova, Tatyana A. Tsvetkova, Artashes V. Karmenyan, Aleksei G. Rebeko, Rudolf Ph. Baum. Novel drug form of chlorin $e_6$//In Optical Methods for Tumor Treatment and Detection: Mechanisms and Techniques in Photodynamic Therapy IX.—T. J. Dougherty, ed., Vol. 3909, 124-129 (2000)).

2. Determination of number of cells after cell monolayer staining with crystal violet at the end of experiment. This method is less laborious and expensive than MTT-test and it also allows to calculate cytotoxic and cytophototoxic indexes of PS (A. E. Medvedev et al., Biomed. Science, 1990, v.1, p. 261), but it is less precise since crystal violet stains dead cells as well.

3. Comparative genotoxic and genophototoxic effect of PS is estimated by the degree of inhibition of DNA synthesis in cells. DNA synthesis is evaluated by the level of incorporation of $^{14}C$ thymidine into DNA, using standard radiometric methods (O. Yu. Abakumova, et. al., J. Neural. Transm. Suppl.3, 1998, V. 52, p. 87).

All of three studied cell lines are highly sensitive to laser irradiation effect after PS treatment (data of MTT-test). According to susceptibility to laser irradiation cell lines range as follows: RGGN1>PC12>Hep27.

At prolonged PS effect in 5 µM concentration on cells in darkness survival was 96.5-86.2% for PC-12, 103.7-93.0% for RGGN1 and 109.7-87.9% for Hep27 (MTT-test-crystal violet, correspondingly). Under the same conditions DNA synthesis in PC-12 cells stayed practically unaffected and it was 21.2 and 22.2% reduced in Hep27 and RGGN1 cells correspondingly. The observable increase in number of RGGN1 and Hep27 cells under effect of 5 µM PS on cells in darkness is most likely related to induction of cells proliferative activity by PS. In general cytotoxic activity is more typical for PS in the absence of irradiation than induction of proliferative activity.

Cell death is observed after laser irradiation of cells treated with PS. Dose-dependent cytophototoxic activity of the preparation is detected and it allows to calculate $EC_{50}$, i.e. to determine the PS concentration at which 50% of cells die. These data are given in Table 2. It should be noted that PS with $EC_{50}$ less than 20 μM are considered to be efficient for tumor growth suppression.

DNA synthesis in PC-12 cells is strongly decreased (96.5% decrease comparing to only irradiated control) at determination of genophototoxicity after treating the cells with 5 μM PS and laser irradiation. DNA synthesis stimulation after laser irradiation at low PS concentrations is observed in Hep27 and RGGN1 cells, this synthesis being considerably reduced in the presence of 5 μM RC. The observable DNA synthesis stimulation may be explained by the fact that transformed liver and glia cells that survived at low PS concentrations possess high ability to synthesize DNA and to regenerate the population.

Thus, PS is a highly cytophototoxic preparation for different types of tumor cells. In high concentrations (>5 μM) it is a moderate inhibitor of tumor growth even without irradiation. Due to high genophototoxicity PS can be considered as a strong tumor growth inhibitor at irradiation.

PS toxic properties were studied in in vivo experiments (Example 14). The average $LD_{50}$ is 210.53±22.2 mg/kg weighting coefficient being considered, and the dose causing the death of 10% of experimental animals ($LD_{10}$) is 169,87 mg/kg. These experiments allow to consider PS as a "Low toxic substance".

PS biodistribution was studied in in vivo experiments (Example 11). The following mechanisms of distribution of compounds are observed when PS is introduced intraperitoneally to mice with T36 embryocarcinoma inoculated into hind leg muscle. After injection PS gets into blood, and then it is redistributed into organs and tissues of an animal (Tab. 3).

As it can be seen in Table 3 tumour accumulation maximum (0,70 μM) is achieved in 5 hours after intraperitoneal injection in a dose of 40 mg/kg and it is conserved for a long period (18-24 hours). Tumoral concentration 18 h after injection is 0.48 μM, that is 1,5 times less than in accumulation absolute maximum at high selectivity of accumulation. The tumour/muscle tissue ratio is 32, and tumour/skin ratio is 44.

Tumour accumulation maximum (0,32 μM) is achieved in 0.5 hours after intravenous injection in a dose of 20 mg/kg and it is also conserved for a long period (up to 5 hours). Maximum contrast of accumulation at intravenous injection is achieved in 3 hours and this value makes 3 for tumor/muscle tissue and 4 for tumor/skin. PS is excreted out of the organism by 98% in a day.

TABLE 2

Lipophily coefficient and in vitro activity of "Radachlorin, 0.5% solution for injections" ("Photochlorin").

| Tests, cell lines | Cytotoxicity ("dark" toxicity), % to control at 5 μM | Photocytotoxicity, $EC_{50}$, μM[1] | (Cd) |
|---|---|---|---|
| MTT test, PC-12 | 96.5 | 1.8 | 1.40 |
| MTT test, RGGN1 | 103.7 | 1.8 | |
| MTT test, Hep27 | 109.7 | 3.9 | |
| Crystal violet test, PC-12 | 86.2 | 1.5 | |
| Crystal violet test, RGGN1 | 93.0 | 1.8 | |
| Crystal violet test, Hep27 | 87.9 | 4.7 | |
| Genotoxicity, PC-12 | 104.7 | 3.5 % to control at 5 μM | |
| Genotoxicity, RGGN1 | 77.8 | 132.2 % to control at 5 μM | |
| Genotoxicity, Hep27 | 78.8 | 100.7 % to control at 5 μM | |

[1]Except for genophototoxicity

The results of the preparation effectiveness estimation at PDT of cancer in in vivo experiments on mice (Example 15) allow to state that "Radachlorin, 0.5% solution for injections" ("Photochlorin") and "Radachlorin, 0.05% gel" possess the expressed photodynamic activity.

The "Liquid extract of chlorins" medicinal substance including chlorins sodium salts (or salts of chlorins and other strong inorganic bases) is used for producing medicinal forms by supplementing different additives approved by RF State Pharmacopoeia: calcium carbonate, saccharose, glucose, starch, magnesium stearate, polyvinylpirrolidones, polyglucans, methylglucamine, isotonic solution, dimethylsulfoxide, gel and water-emulsion substrates etc. (Examples 4-9).

Ointments, liniments, gels, oil-based preparations are used for external use, these forms contain the substrates approved by RF State Pharmacopoeia, 5-20% of dimethylsulfoxide and 0.5-12% of "Liquid extract of chlorins" substance, or 0.8-14% of "Liquid extract of chlorins" substance and 86-99.2% of dimethylsulfoxide (Examples 8, 9).

Dimethylsulfoxide concentrations range in combination with substrates is explained by the fact that substance penetration into tissues is low at concentration less than 5%, and that reduces the PDT effectiveness. If dimethylsulfoxide concentration is higher than 20% medicinal forms on other bases lose their stability at storage. Substance concentrations range is explained by the fact that if this concentration is less than 0.5% substance concentration in tissue is insufficient for effective PDT. If substance concentration is higher than 12% tissue loses transparence for light radiation, all light is absorbed in the upper layer of the tissue that results in a burn at low effectiveness of PDT procedure.

TABLE 3

| | The main pharmacokinetic parameters | | | | | | | |
|---|---|---|---|---|---|---|---|---|
| PS | Absolute accumulation maximum, organ-μM-hour | Tumour accumulation maximum, μM-hour | Tumour/skin ratio at tumour accumulation maximum | Tumour/muscles ratio at tumour accumulation maximum | Tumour accumulation at contrast maximum, μM-hour | Tumour/skin ratio at contrast maximum | Tumour/muscles ratio at contrast maximum | Excretion, %---hour |
| Photochlorine intravenous, 20 mg/kg | small intestines - 4.0-0.5 | 0.32-0.5 | 6.4 | 1.6 | 0.29-3 | 14.5 | 2.9 | 98---24 |
| Photochlorine intraperitoneally, 40 mg/kg | blood - 5.2-0.5 | 0.70-5 | 3.9 | 3.0 | 0.48-18 | 44.0 | 32.0 | 98---24 |

Substance exposition on skin before irradiation is 0.5-24 hours at external use. The substance has no time to penetrate into a tissue on necessary depth in time less than 0,5 hours. If time interval is more than 24 hours the fall of preparation absolute accumulation value is observed due to its redistribution and excretion. Besides, long-time expositions of external medicinal forms on a skin are inconvenient from the clinical point of view.

The preparation is used for intravenous dropwise or stream introduction in the form of 0.1-1% solutions in any mediums approved by RF State Pharmacopoeia (apyrogenic water for injections, dimethylsulfoxide, saline solution, etc.). Use of solutions of the substance with concentration less than 0.1% is irrational considering volumes of liquid introduced into an organism. Use of solutions with concentration higher than 1% is impossible due to the low filterability of such solutions at a stage of sterilisation through antibacterial filters.

Semiconductor laser diode module for photodynamic therapy ML-662-SP designed by ZAO "MYLON" (Saint Petersburg) and OOO "SIGM PLUS" (Moscow) is used for activation of PS "Liquid extract of chlorins" substance. This module has the following output data (Certificate of the Russian Ministry of Health, Reg. No. 29/10-679-96):

power of 2,5-3 W in a fibre of 200 microns with the aperture 0.22.

high intensive laser diodes of "Polaroid" corporation (USA) and OOO "SIGM PLUS" coproduction with maximum irradiation wavelength of 662±3 nm.

Modules of a lower power (with a lower number of diodes) with maximum irradiation wavelength of 662±3 nm may be used for activation of PS substance, the solid-state laser with pumping on a second harmonic of yttrium-aluminium garnet YAG:Nd$^{3+}$ with maximum irradiation wavelength of 670 nm may be used also.

Magnitude of fed energy varies from 30 up to 3000 J. At light doses less than 30 J the PDT procedure becomes excessively long since scanning should be realised at the extremely small areas in order to achieve the optimal effect. At light doses more than 3000 J and tumour dimensions most frequently occurring in clinical practice the considerable damage of healthy tissue leading to prolongation of regeneration period is observed.

Surface density of fed energy varies from 50 up to 2500 J/cm$^2$. At surface light doses less than 50 J/cm$^2$ no effect is observed. At surface light doses more than 2500 J/cm$^2$ the considerable damage of healthy tissue leading to prolongation of regeneration period is observed.

The range of wavelengths of exciting radiation is connected to a technical characteristic of the used laser (662±3 nm), shift of the preparation absorption maximum depending on polarity of medium (654-662 nm) and the content of purpurin 5 in the substance (5-20%, half-width of a long-wavelength absorption band at 663-670 nm) (Tab. 1).

EXAMPLE 1

Description of the Physicochemical Properties of PS

PS represents dense black mass, acquiring a green shade in a thin layer, with an odour of algae.

In order to confirm authenticity of PS properties "Liquid extract of chlorins", 7.5% is thoroughly stirred, a portion of the extract (1 mg) is dissolved in 10 ml of medical or the most purified rectified ethyl alcohol, 95%, and optical density is measured at 662 nm (D). The value is 0,23. The molecular extinction $\epsilon$ (M$^{-1}$cm$^{-1}$) is calculated according to the formula $\epsilon=D*597/(0,004)$. The resulting value should lie within the range of 33300-35100. After substitution, $\epsilon=0,23*597/(0,004)=34328$. Hence, "Liquid extract of chlorins" contains 7.5% PS.

PS solution in ethyl alcohol has yellow-green colour. The solution acquires ruby-red colouring if light rays from the medical blue lamp MDS 220-75 (technical specifications 16.535.376-79) are passed through the solution layer in the light-protected place.

For the quantitative determining "Liquid extract of chlorins" is thoroughly stirred, a portion of the extract (5 mg) is dissolved in 10 ml of medical or the most purified rectified ethyl alcohol, 95%, and optical density is measured at 662 nm (D). The value is 2,15. PS content is calculated according to the formula: c,%=(D*597*10*100)/(34230*5). The resulting value should correspond to the specified. After substitution, c,%=(2,15*597*10*100)/(34230*5)=7,5% (corresponds to the specified).

For the further analyses dilute hydrochloric acid solution is added to 100 mg of "Liquid extract of chlorins" till PS precipitates, the precipitate is filtered out, dried in vacuum over phosphorus pentoxide for 12 h and PMR-, mass spectrums and absorption spectrum are taken in the wavelength range of 360-720 nm.

PS PMR spectrum (FIG. 6): (in DMSO-D6, conc. solution): 9.64, 9.55, 9.52, 9.39, 8.90, 8.79 (s, meso-$\underline{H}$ of chlorin e$_6$ and purpurin 5), 8.09, 8.04, 7,97, 7.92 (2d, C$\underline{H}$=CH$_2$ of chlorin e$_6$ and purpurin 5), 6.84 (s, γ-meso-C$\underline{H}$O of purpurin 5), 6.37, 6.32, 6.13, 6.10 (2d, CH=C$\underline{H}_2$), 5.43 (2s, γ-meso-C$\underline{H}_2$COOH), 4.60 (m, 7-$\underline{H}$), 4.45 (m, 8-$\underline{H}$), 3.80, 3.56 (q×2, 4-C$\underline{H}_2$CH$_3$), 3.75, 3.64, 3.51, 3.46, 3.29, 3.23 (c, nuclear C$\underline{H}_3$ of chlorin e$_6$ and purpurin 5), 2.38, 2.32 (2m, 7-C$\underline{H}$CH$_2$CH$_2$COOH), 2.71, 2.20 (2m, 7-CH$_2$C$\underline{H}_2$COOH), 1.76 (d, 8-C$\underline{H}_3$), 1.72 (t, 4-CH$_2$C$\underline{H}_3$),-1.63,-1.91 (2s, 2N$\underline{H}$) ppm.

PS mass spectrum (FIG. 7): e.i., M$^+$ (%), 596 (16.0), 566 (9.4), 508 (100.0), 494 (7.3), 447 (9.4), 435 (50.6), 421 (12.8), 405 (6.9), 254 (7.4).

PS visible absorption spectrum: λ ($\epsilon$) (ethanol), 386 (22310), 406 (113040), 506 (14870), 536 (8925), 608 (7437), 662 (34220).

According to PMR spectrum the substance contains 80% of chlorin e$_6$, 15% of purpurin 5 and 5% of purpurin 18 (minor signals at 9.25, 9.10, 8.71, 7.84, 3.55, 3.32, 3.04 ppm), that corresponds to a composition being patented. According to the mass spectrum there are peaks of molecular ions 596 of chlorin e$_6$ and 566 of purpurin 5. In absorption spectrum there is a band of 662 nm with the absorption value that is well matching the molecular extinction of PS etalon (34230).

Hence, the studied sample is "Liquid extract of chlorins", 7.5%.

EXAMPLE 2

Producing PS as "Liquid Extract of Chlorins", 6.5%

*Spirulina* biomass (2 kg) is treated with acetone (3×2 L) till chlorophyll a is completely extracted, the biomass is filtered out, the extract is treated with hydrochloric acid (30 ml) in order to remove magnesium ion out of the chlorophyll molecule, the extract is neutralised and precipitated pheophytin a (8 g) is filtered out, then pheophytin a is hydrolysed in the mixture of hydrochloric acid-acetone-hexane, for this purpose pheophytin a is dissolved in the mixture of 50 ml of acetone, 5 ml of hexane and 40 ml of hydrochloric acid (37%), the mixture is heated up to 40° C. and stirred for 1 hour, then hexane (50 ml) is added and organic phase is washed with the mixture of acetone and hydrochloric acid (2:1, 3×50 ml), water phase is washed with hexane (5×40 ml), then water phase containing pheophorbide a is neutralised with excess of sodium citrate (tri-, di- or mono-substituted) water solution, precipitated pheophorbide a is filtered out, washed with water (3×50 ml), recrystallised out of the acetone-water mixture, air dried till its mass becomes constant (pheophorbide a yield is 4.2 g, 7.1 mM, 77%), then pheophorbide a (2.7 g, 4.56 mM) is dissolved in acetone (100 ml), strong inorganic base is added in the form of water solution (0.05%, 25 ml), stirred at 60° C. for 5 min, extra volume of inorganic base is added in the form of water solution (20%, 25 ml), the mixture is heated at 40° C. for 90 min, neutralised with diluted hydrochloric acid (2%, about 250 ml), chlorin $e_6$ precipitate is separated by centrifugation, washed with distilled water (5×10 ml) till acid reaction disappears, 1.85 g (2.96 mM, 65%) chlorin $e_6$ is obtained, then chlorin $e_6$ is recrystallised out of acetone in order to separate linear tetrapyrroles, chlorin $e_6$ is filtered out and washed three times with distilled water, chlorin $e_6$ is heated in sealed reservoir at the temperature of 40° C. for 30 days, then it is cooled and 1% sodium hydroxide solution is added till pH 7.5, the resulting PS contains 15% of purpurin 5, 80% of chlorin $e_6$ and 5% of purpurin 18 (chlorin $p_6$), then PS solution is adjusted with distilled water to make photosensitizer concentration 6.5%, giving 14.2 g (50%) PS in the form of 6.5% "Liquid extract of chlorins".

The resulting "Liquid extract of chlorins" PMR spectrum (FIG. 6): (in DMSO-D6, conc. solution): 9.64, 9.55, 9.52, 9.39, 8.90, 8.79 (s, meso-$\underline{H}$ of chlorin $e_6$ and purpurin 5), 8.09, 8.04, 7.97, 7.92 (2d, C$\underline{H}$=CH$_2$ of chlorin $e_6$ and purpurin 5), 6.84 (s, γ-meso-C$\underline{H}$O of purpurin 5), 6.37, 6.32, 6.13, 6.10 (2d, CH=C$\underline{H}_2$), 5.43 (2s, γ-meso-C$\underline{H}_2$COOH), 4.60 (m, 7-$\underline{H}$), 4.45 (m, 8-$\underline{HH}$), 3.80, 3.56 (q×2, 4-C$\underline{H}_2$CH$_3$), 3.75, 3.64, 3.51, 3.46, 3.29, 3.23 (s, nuclear C$\underline{H}_3$ of chlorin $e_6$ and purpurin 5), 2.38, 2.32 (2m, 7-C$\underline{H}_2$CH$_2$COOH), 2.71, 2.20 (2m, 7-CH$_2$C$\underline{H}_2$COOH), 1.76 (d, 8-C$\underline{H}_3$), 1.72 (t, 4-CH$_2$C$\underline{H}_3$),-1.63,-1.91 (2s, 2N$\underline{H}$) ppm.

The substance contains 80% of chlorin $e_6$, 15% of purpurin 5 and 5% of purpurin 18 (chlorin $p_6$) (signals at 9.25, 9.10, 8.71, 7.84, 3.55, 3.32, 3.04 ppm).

The resulting substance mass spectrum (FIG. 7): e.i., M$^+$ (%), 596 (16.0), 566 (9.4), 508 (100.0), 494 (7.3), 447 (9.4), 435 (50.6), 421 (12.8), 405 (6.9), 254 (7.4).

Visible absorption spectrum (FIG. 8): λ(ε) (ethanol), 386 (22320), 406 (113110), 506 (14880), 536 (8930), 608 (7440), 662 (34230).

EXAMPLE 3

Producing PS as "Liquid Extract of Chlorins", 7.5%

*Spirulina* biomass (2 kg) is treated with acetone (3×2 l) till chlorophyll a is completely extracted, the biomass is centrifuged out, the extract is treated with hydrochloric acid (30 ml) in order to remove magnesium ion out of the chlorophyll molecule, the extract is neutralised and precipitated pheophytin a (8 g) is filtered out, then pheophytin a is hydrolysed in the mixture of hydrochloric acid-acetone-hexane, for this purpose pheophytin a is dissolved in the mixture of 100 ml of acetone, 50 ml of hexane and 80 ml of hydrochloric acid (37%), the mixture is heated up to 60° C. and stirred for 20 min, then hexane (100 ml) is added and organic phase is washed with the mixture of acetone and concentrated hydrochloric acid (5:1, 3×50 ml), water phase is washed with hexane (5×40 ml), then water phase containing pheophorbide a is neutralised with excess of sodium citrate (tri-, di- or mono-substituted) water solution, precipitated pheophorbide a is filtered out, washed with water (3×50 ml), recrystallised out of the acetone-water mixture, air dried till its weight becomes constant (yield is 3.8 g, 6.4 mM, 67%), then pheophorbide a (2.7 g, 4.56 mM) is dissolved in acetone (100 ml), strong inorganic base is added in the form of water solution (1%, 25 ml), stirred at 30° C. for 30 min, extra volume of strong inorganic base is added in the form of water solution (20%, 25 ml), the mixture is heated at 60° C. for 20 min, neutralised with diluted hydrochloric acid (2%, about 250 ml), chlorin $e_6$ precipitate is separated by centrifugation, washed with distilled water (5×10 ml) till acid reaction disappears, 1.67 g (2.67 mM, 55%) chlorin $e_6$ is obtained, then chlorin $e_6$ is recrystallised out of acetone in order to separate linear tetrapyrroles, chlorin $e_6$ is filtered out and washed three times with distilled water, chlorin $e_6$ is heated in sealed reservoir at the temperature of 100° C. for 1 hour, then it is cooled and 1% potassium hydroxide solution is added till pH 8.5, the resulting PS contains 2% of purpurin 5, 82% of chlorin $e_6$ and 16% of purpurin 18 (chlorin $p_6$), then PS solution is adjusted with distilled water to make photosensitizer concentration 7.5%, giving 11.1 g (50%) PS in the form of 7.5% paste.

The resulting substance spectra are similar to those given in Example 2 and represent a superposition of spectra of chlorin $e_6$ (FIG. 9-11) and purpurin 5 (FIG. 12-14).

EXAMPLE 4

A Special Case of Producing PS—Producing "Liquid Extract of Chlorins", 7.5%

PS containing 2% of purpurin 5, 82% of chlorin $e_6$ and 16% of purpurin 18 (chlorin $p_6$) in the form of 7.5% paste described in the previous Example is gel filtrated on a Sephadex G10 column of 50 mm diameter and 100 mm height with the use of 1% potassium hydroxide solution as an eluent, till chlorin $e_6$ content becomes 90%, purpurin 5-5% and purpurin 18-5%. Diluted hydrochloric acid solution is added till PS precipitates, PS is adjusted with apyrogenic water for injections to make photosensitizer concentration 7.5% $_{mass}$ giving 6.8 g "Liquid extract of chlorins", 7.5%. An electron spectrum of the product—see. FIG. 8.

EXAMPLE 5

A Special Case of Producing PS—Producing the "Radachlorin, 0.1% Solution for Injections" Medicinal Form After gel filtration diluted hydrochloric acid solution is added to the solution of PS described in Example 4 till PS precipitates, this precipitate is filtered out, concentrated sodium hydroxide solution in apyrogenic water for injections is added till pH 7,5 and apyrogenic water for injections is added to make PS concentration 0.1%, then bacteria are filtered off the solution through antibacterial "Millipore" microporous filter with 0,22 μm pores. The yield is 500 ml of the solution. An electron spectrum of the product—see. FIG. 8.

EXAMPLE 6

A Special Case of Producing PS—Producing the "Radachlorin, 0.5% Solution for Injections" ("Photochlorin") Medicinal Form After gel filtration diluted hydrochloric acid solution is added to the solution of PS described in Example 4 till PS precipitates, this precipitate is filtered out, concentrated potassium hydroxide solution is added till pH 7, then the solution is adjusted with N-methyl-D-glucamine up to pH 8,5 under pH-meter control, apyrogenic water for injections is added to make photosensitizer concentration 0.5% $_{mass}$, then bacteria are filtered off the solution through antibacterial "Millipore" microporous filter with 0,22 μm pores. The yield is 100 ml of the solution. An electron spectrum of the product—see. FIG. 8.

EXAMPLE 7

A Special Case of Producing PS—Producing the "Radachlorin, 1% Solution for Injections" Medicinal Form After gel filtration diluted hydrochloric acid solution is added to the solution of PS described in Example 4 till PS precipitates, this precipitate is filtered out, concentrated sodium hydroxide solution is added till pH 8,5 then apyrogenic water for injections is added to make photosensitizer concentration 1% $_{mass}$, then bacteria are filtered off the solution through antibacterial "Millipore" microporous filter with 0,22 μm pores. The yield is 50 ml of the solution. An electron spectrum of the product—see. FIG. 8.

EXAMPLE 8

A Special Case of Producing PS—Producing the "Radachlorin, Gel" Medicinal Forms

After gel filtration diluted hydrochloric acid solution is added to the solution of PS described in Example 4 till PS precipitates, this precipitate is centrifuged out, adjusted with apyrogenic water for injections to make photosensitizer concentration 6.5% $_{mass}$, then the following variants are realised:

Variant (a). 0,3 g of Pemulen TR1 or Carbopol 2020 (BF Goodrich, UK) are added to 75 ml of water and 5 g of dimethylsulfoxide at room temperature and stirred for ¼-8 hours. Water alkaline solution is added till pH 5. Gel is resuspended supplementing "Liquid extract of chlorins", 6.5% and water to make 0.05% concentration of chlorin $e_6$ in resulting gel, gel is vacuumised for 5 minutes at 10-50 mm Hg. The yield is 100 g of the gel.

Variant (b). 5 g of dimethylsulfoxide and "Liquid extract of chlorins", 6.5% is added to 70 ml of water to make 0.05% concentration of chlorin $e_6$ in resulting gel, then 15 g of Aculyn 33A (ISP, USA) is added. The substance is stirred to homogeneity and water alkaline solution is added till pH 5. Gel is vacuumised for 5 minutes at 10-50 mm Hg. The yield is 100 g of the gel.

After gel filtration diluted hydrochloric acid solution is added to the solution of PS described in Example 4 till PS precipitates, this precipitate is centrifuged out, adjusted with apyrogenic water for injections to make photosensitizer concentration 7.5% $_{mass}$, then the following variants are realised:

Variant (c). 0,7 g of Pemulen TR1 or Carbopol 2020 (BF Goodrich, UK) are added to 60 ml of water and 20 g of dimethylsulfoxide at room temperature and stirred for ¼-8 hours. Triethanolamine water solution is added till pH 8.5. Gel is resuspended supplementing "Liquid extract of chlorins", 7.5% and water to make 1% concentration of chlorin $e_6$ in resulting gel, gel is vacuumised for 5 minutes at 10-50 mm Hg. The yield is 100 g of the gel.

Variant (d). 20 g of dimethylsulfoxide and "Liquid extract of chlorins", 7.5% is added to 55 ml of water to make 1% concentration of chlorin $e_6$ in resulting gel, then 15 g of Aculyn 33A (ISP, USA) is added. The substance is stirred to homogeneity and triethanolamine water solution is added till pH 8.5. Gel is vacuumised for 5 minutes at 10-50 mm Hg. The yield is 100 g of the gel.

EXAMPLE 9

A Special Case of Producing PS—Producing the "Radachlorin, Dimethylsulfoxide Solution for External Use" Medicinal Forms Variant (a). After gel filtration in Example 4 diluted hydrochloric acid solution is added to the mixture till PS precipitates, this precipitate is filtered out, adjusted with apyrogenic water for injections to make PS concentration 7.5% $_{mass}$, and 14 g of the resulting "Liquid extract of chlorins" is added to 86 g of dimethylsulfoxide at room temperature to make 1% concentration of chlorin $e_6$ in the resulting solution, and stirred to homogeneity. The yield is 100 g of the solution.

Variant (b). After gel filtration in Example 4 diluted hydrochloric acid solution is added to the mixture till PS precipitates, this precipitate is filtered out, adjusted with apyrogenic water for injections to make PS concentration 7.5% $_{mass}$, and 0.8 g of the resulting "Liquid extract of chlorins" is added to 99.2 g of dimethylsulfoxide at room temperature to make 0.05% concentration of chlorin $e_6$ in the resulting solution, and stirred to homogeneity. The yield is 100 g of the solution.

EXAMPLE 10

For purpurin 5 identification the reaction mixture of Example 2 is gel filtrated on a Sephadex G10 column with the use of 1% N-methyl-D-glucamine solution as an eluent to give 3 fractions, the first and the second fractions contain purpurin 5. These fractions are neutralised, a precipitate is filtered out, dissolved in chloroform-methanol 1:1 mixture and esterified with diazomethane. The mixture is washed with water, an organic phase is separated, dried with anhydrous magnesium sulfate, concentrated by evaporation in vacuum and chromatographed on silica gel Merck, Kieselgel, 0,04-0, 063, the last (least mobile) fraction is collected. If necessary the resulting purpurin 5 dimethyl ester (10,1% calculating to the dry reaction mass taken for esterification) is chromatographed repeatedly.

PMR spectrum (FIG. 15): (DMSO-D6, conc. solution): 9.64, 9.46, 8.82 (s, meso-$\underline{H}$), 8.06 (2d, C$\underline{H}$H=CH$_2$), 6.82 (s, γ-meso-C$\underline{H}$O), 6.34, 6.31, 6.19, 6.16 (2d, —CH=C$\underline{H}_2$), 4.54 (m, 7-$\underline{H}$), 4.46 (m, 8-$\underline{H}$), 3.61 (q, 4-C$\underline{H}_2$CH$_3$), 4.20, 3.81, 3.57, 3.53, 3.47 (5s, —COOC$\underline{H}_3$ and nuclear —C$\underline{H}_3$), 2.38, 2.35 (2m, 7-C$\underline{H}_2$CH$_2$COOH), 2.68, 1.85, (2m, 7-CH$_2$C$\underline{H}_2$COOH), 1.73 (d, 8-C$\underline{H}_3$), 1.70 (t, 4-CH$_2$C$\underline{H}_3$) ppm.

Mass spectrum (FIG. 16): e.i., M$^+$ (%), 594 (8.6), 566 (100.0), 505 (5.1), 491 (9.8), 475 (8.2), 463 (1.7), 447 (1.4), 433 (1.7), 403 (2.0), 262 (5.0).

Visible absorption spectrum (FIG. 17): λ(ε) (chloroform), 408 (117200), 501 (11380), 542 (9830), 617 (6720), 668 (35200).

Purpurin 5 dimethyl ester is dissolved in acetone and concentrated hydrochloric acid (37%) is added in the ratio 1:2. The mixture is stirred for 2 hours at 25° C., neutralised, purpurin 5 is filtered out, washed with water, dissolved in 10% N-methyl-D-glucamine solution and gel filtrated on a Sephadex G10 column with the use of 1% N-methyl-D-glucamine solution as an eluent, the second fraction is collected, neutralised, a precipitate is filtered out, washed with water, dried over phosphorus pentoxide till the weight becomes constant to give purpurin 5 (5,2% calculating to the dry reaction mass taken for esterification).

PMR spectrum (FIG. 12): (DMSO-D6, conc. solution): 9.55, 9.39, 8.79 (s, meso-$\underline{H}$, 8.09, 8.04, 7.97, 7.92 (2d, —C$\underline{H}$=CH$_2$), 6.84 (s, γ-meso-C$\underline{H}$O), 6.37, 6.32, 6.13, 6.10 (2d, —CH=C$\underline{H}_2$), 4.60 (m, 7-$\underline{H}$), 4.45 (m, 8-$\underline{H}$), 3.55 (q, 4-C$\underline{H}_2$CH$_3$), 3.75, 3.46, 3.23 (s, nuclear-C$\underline{H}_3$), 2.38, 2.32 (2m, 7-C$\underline{H}_2$CH$_2$COOH), 2.71, 2.20 (2m, 7-CH$_2$C$\underline{H}_2$COOH), 1.76 (d, 8-C$\underline{H}_3$). 1.72 (t, 4-CH$_2$C$\underline{H}_3$) ppm.

Mass spectrum (FIG. 13): e.i., M$^+$ (%), 566 (8.2), 494 (100.0), 447 (9.1), 435 (49.6), 421 (12.7), 405 (6.6), 254 (7.1).

Visible absorption spectrum (FIG. 14): λ (ε) (ethanol), 408 (116900), 501 (11320), 540 (9790), 615 (6710), 665 (35090).

EXAMPLE 11

Study of Pharmacokinetics and Metabolism of the "Liquid Extract of Chlorins" Substances and the "Radachlorin, 0.5% Solution for Injections" ("Photochlorin") Medicinal Form 769,2 mg/kg of 6.5% "Liquid extract of chlorins" substance from the Example 2 (50 mg/kg calculating to anhydrous chlorins substance) were introduced intraperitoneally to mice of the line Balb/c. The mice were slaughtered 3 hours after injection (each group consisted of 3 mice). The materials of liver, kidney, spleen, lungs, small intestines, tumor, surrounding muscle tissue as well as from blood, urine, faeces from large intestine weighing 100 mg each were thoroughly homogenised in glass homogenizers supplementing 4 ml of saline solution. For examination of biological fluids (blood, urine) 0,1 ml of each fluid were taken with subsequent dissolution in 4 ml of saline solution. The resulting homogenates were studied on "Perkin-Elmer" spectrofluorimeter (MPF-44A model).

Study of the "Radachlorin, 0.5% solution for injections" ("Photochlorin") medicinal form was carried out in a similar way in homogenates of organs and tissues of mice to whom the preparation was introduced intraperitoneally in the dose of 50 mg/kg, the animals were slaughtered 3 h after injection.

In both cases there is a shift of fluorescence intensity maximum in tissues of liver, small intestines, spleen and kidney to 670 nm (by 10-12 nm comparing to 0,01M borate buffer solution, pH 9.2, and by 5-6 nm comparing to 0,01M borate buffer solution, pH 9.2, with 1% of human serum albumine), that indicates the metabolism of "Radachlorin, 0.5% solution for injections" ("Photochlorin") (FIG. 5).

In fluorescence spectrum this phenomenon looks differently, than a simple spectrum widening and shift to the long-wavelength range due to effect of hydrophoby of medium (for example, after a hydrophobic interaction with proteins, lipoproteins). Shift of intensity maximum is observed without or with a little widening of a band that is typical of formation of a new compound. Fluorescence spectra of purpurin 5 in 0,01M borate buffer solution, pH 9.2, with 1% of human serum albumin are characterised by presence of 670 nm band.

In blood, pulmonary parenchyma, as well as in skin and tumour the widening of spectra 1,4-1,5 times at wavelength of 669 nm is observed, that indicates the presence of "Radachlorin, 0.5% solution for injections" ("Photochlorin") (its complex with proteins) and a metabolite mixture in homogenates.

If "Radachlorin, 0.5% solution for injections" ("Photochlorin") is added directly to the tubes with homogenates of intact animals tissues in concentrations of 0.5-1.0 μM a metabolite of "Radachlorin, 0.5% solution for injections" ("Photochlorin") is detected in blood, small intestines, liver, spleen and lung (a shift to long-wavelength range without widening of a spectrum), and only in skin homogenate a slight 1,15 times increase in spectrum half-width is observed, that indicates the presence of "Photochlorin"—metabolite mixture in a sample.

If "Radachlorin, 0.5% solution for injections" ("Photochlorin") concentration in homogenates of organs is increased to 5-10 μM, the presence of chlorine e$_6$-purpurin 5 mixture is registered practically in all the samples (a shift of spectra to long-wavelength range at 1,15-1,05 times increase in half-width of spectra).

Thus, it is possible to consider that formation of a metabolite at "Radachlorin, 0.5% solution for injections" ("Photochlorin") addition to homogenates depends on concentration of the preparation and activity of enzymes of a homogenised tissue.

These experiments clearly demonstrate the conversion of chlorin e$_6$ into purpurin 5 under in vivo and ex vivo conditions. This conversion is similar to the conversion of chlorin e$_6$ into purpurin 5 at heating.

EXAMPLE 12

N-Octanol/Phosphate Buffer, pH 7.4, Distribution Coefficient 300 ml of n-octanol and 300 ml of phosphate buffer, pH 7.4, are vortexed for 20 sec and centrifuged for 10 min at 10000 rpm for splitting. 0.1 ml PS aliquot with PS concentration of 5 mg/ml is dissolved in prepared buffer solution (2 ml) and n-octanol (8 ml), absorption maximum is determined at 406 nm.

The values of $D°_c$, and $D^b_c$ are obtained, where o is n-octanol, b is phosphate buffer, c is control. Equilibrium n-octanol/phosphate buffer distribution is achieved by vortexing of 2 ml of phosphate buffer and 8 ml of n-octanol with 0.1 ml of PS for 20 sec at 20° C. with subsequent centrifugation for 10 min at 10000 rpm. Optical density of each phase is measured at 406 nm giving the values of $D°$ and $D^b$, where o is n-octanol, b is phosphate buffer.

$C_d$ is calculated according to the formula:

$C_d = (D° V° D°_c V°_c)/(D^b V^b D^b_c V^b_c)$, where $V°$—the volume of octanol taken for determination of equilibrium distribution (8 ml), $V°_c$—the volume of octanol, saturated with water, taken for control determination of aliquot absorption (8 ml), $V^b$—the volume of the buffer taken for determination of equilibrium distribution (2 ml), $V^b_c$—the volume of the buffer, saturated with octanol, taken for control determination of aliquot absorption (2 ml). Experiment is carried out for three times and the obtained values of $C_d$ are averaged.

The resulting value is 1.4±0.3.

EXAMPLE 13

Determination of in vitro Phototoxicity (Biological Activity) and Cytotoxicity (Cell Toxicity) of the "Radachlorin, 0.5% Solution for Injections" ("Photochlorin") Medicinal Form For this work the laminar "Flow Lab" (UK), the CO$_2$-incubator "Flow Lab" (UK), the multiscan "Bio-Tek Instruments" (USA), mediums and serums "PanEco" (Russia) are used.

For one experiment cells of one line are passed in two 48-cell plates: one for laser irradiation and one for the "dark" experiment. Next day the preparation is added to the confluent state cells and the plates are thermostated in a black paper. The preparation concentrations of 0.1, 0.5, 2.0 and 5.0 μM are studied. 3 hours after addition of the preparation the cells are irradiated with laser, the exposition irradiation dose being 50 J/cm$^2$, and 39 hours later the MTT-test is carried out as well as incubation with $^{14}$C-thymidine for estimation of DNA synthesis (the "dark" tray is tested too). In all the cases the upper part of the plate is used for the MTT-test, and the lower part is used for measurement of DNA synthesis and number of cells after staining with crystal violet.

The data represented in Tab. 2 are the mean of 4 parallel experiments.

EXAMPLE 14

In vivo Study of Toxic Properties of the "Liquid Extract of Chlorins" Substance and the "Radachlorin, 0.5% Solution for Injections" ("Photochlorin") Medicinal Form Toxicity is studied at intravenous injection of PS to laboratory white mice weighing 19-21 g (nursery of the Russian Academy of Medical Sciences, Krukovo). The animals are kept under standard vivarium conditions and are fed according to the Ministry of Health of the USSR Order No 1179 of 10.10.83 "About the approval of specifications of forage expenditures for laboratory animals in health protection institutions". Toxicity is determined according to the animal death, after calculation of the mean lethal dose—$LD_{50}$. The calculation is carried out according to statistical methods recommended by the State Pharmacopoeia, edition XI (1,3). On the basis of $LD_{50}$ the studied preparation is referred to the specific class of toxicity according to Hodge and Sterner. The intoxication reactions are also registered during the experiment.

12 mice (6 male and 6 female) are used for each PS dose being tested. The following doses are used for determination of PS $LD_{50}$: 5, 10, 15, 20, 30, 40, 50, 75, 100, 125, 150, 175, 200, 225, 250, 275 mg/kg. The solution with 5 mg/ml PS concentration is introduced to mice intravenously, a dose is varied by the volume of introduced PS.

The resulting $LD_{50}$ value is 210.53±22.2 mg/kg, $LD_{10}$ value is 169.87 mg/kg.

EXAMPLE 15

In vivo Biological Activity With the Use of the "Radachlorin, 0.5% Solution for Injections" ("Photochlorin") Medicinal Form Photodynamic activity of the "Radachlorin, 0.5% solution for injections" ("Photochlorin") medicinal form is studied on mice of the line Balb/c with T36 embryocarcinoma inoculated into hind leg muscle. Mice weight is 20-21 g. The irradiation procedure is realised with the diode laser ML-662-SP 2 weeks after inoculation of a tumour. Skin in the irradiation area is depilated before the procedure.

The preparation is introduced intraperotoneally in a dose of 40 mg/kg, that corresponds to a sufficient therapeutic dose. For carrying out the irradiation procedure the mice are etherised. The weight of tumours in control and experimental groups at the moment of experiment varies from 0.9 up to 1 g. Irradiation is carried out 5-6 hours after injection of PS. Every animal, except for control, is irradiated once, then it is observed during a month after the procedure, the area of tumor necrosis and general physiological state are registered.

The average density of exposition dose of irradiation is 150 or 300 $J/cm^2$.

The best results in the form of the complete tumour necrosis, crust formation in 1 week after PDT and this crust dropout in 1.5 months after PDT are observed in the group that obtained the light dose of 300 $J/cm^2$.

EXAMPLE 16

Treatment of a Basal Cell Skin Cancer With the Use of the "Radachlorin, 0.5% Solution for Injections" ("Photochlorin") Medicinal Form The basal cell skin cancer is diagnosed at cytologic examination of a scrape. The preparation is introduced dropwise intravenously to make the concentration of 0,7 mg/kg of patient's weight after dilution in 100 ml of 0,9% sterile NaCl saline solution. In 2-3 hours the irradiation of a tumour with the diode laser ML-662-SP with wavelength of 662 nm with the surface dose of 50 $J/cm^2$ is carried out without anaesthesia. No undesirable side reactions are registered during injection of the preparation and laser irradiation. In 2 hours after irradiation a dark brown focus with surrounding redness zone of 1-2 cm is formed in the place of the tumour. To the end of the first day a necrosis is formed in the place of the tumour in the form of a dry dark brown crust (eschar). In 2-3 weeks the crust rejection takes place, and 2 weeks later the full epithelisation of skin defect in the place of former basalioma takes place with good cosmetic effect.

EXAMPLE 17

Treatment of a Basal Cell Skin Cancer With the Use of the "Radachlorin, 0.05% Gel" Medicinal Form The basal cell skin cancer is diagnosed at cytologic examination of a scrape. The gel is applied over a tumour in thin layer, if possible healthy part of skin is not touched. The irradiation is carried out 20-40 minutes after applying the gel. The irradiation procedure is realised with the diode laser ML-662-SP ("Mylon-Sigm Plus", Russia) with wavelength of 662 nm. The density of the exposition dose of irradiation is 2500 $J/cm^2$. In 2 hours after irradiation a dark brown focus with surrounding redness zone of 1-2 cm is formed in the place of the tumour. In 1 week a necrosis is formed in the place of the tumour in the form of a dry dark brown crust (eschar). In 2 weeks the crust rejection takes place, and 2 weeks later the full epithelisation of skin defect in the place of former basalioma takes place with good cosmetic effect.

EXAMPLE 18

Removing of a Tattoo With the Use of the "Radachlorin, 0.5% Solution in Dimethylsulfoxide for External Use" Medicinal Form The solution is applied to the napkin and the latter is put over the tattoo, covered with black paper or thin aluminium foil and fixed for 30 min. The excess of the solution is removed from a surface with cotton wetted with alcohol. The irradiation procedure is realised with the diode laser ML-662-SP ("Mylon-Sigm Plus", Russia) with wavelength of 662 nm, irradiation is being carried out along the pattern lines trying to avoid affecting the surrounding tissue. The density of the exposition dose of irradiation is 120 $J/cm^2$. In 1 hour after irradiation, skin redness and swelling is observed in the place of the tattoo. To the end of the second day a dark brown "picture" with surrounding redness zone of 1 mm is formed. In 2 weeks a necrosis is formed in the place of the tattoo in the form of a dry dark brown crust. 2 weeks later the peeling of the crust together with the tattoo takes place. At smaller light doses the procedure goes without necrosis by stain decolorisation, but there is a need in repeated sessions in this case. A soft pink tissue is formed in the place of the tattoo in 6 weeks as a result of PDT, this tissue slightly differing from the surrounding skin, the good cosmetic effect is observed.

The invention is claimed is:

1. A method for producing a photosensitizer that includes an alkali metal salt of chlorin, wherein chlorin is composed of chlorin $e_6$ (13-carboxy-17-[2-carboxyethyl]-15-carboxymethyl-17, 18-trans-dihydro-3-vinyl-8-ethyl-2,7,12,18-tetramethylporphyrin)

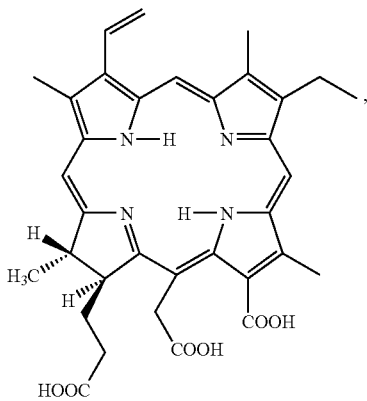

purpurin 5 (13-carboxy-17-[2-carboxyethyl]-15-formyl-17, 18-trans-dihydro-3-vinyl-8-ethyl-2,7,12,18-tetramethylporphyrin)

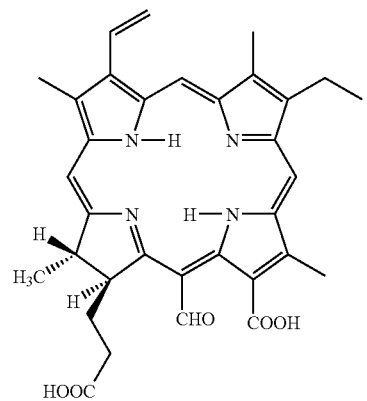

and purpurin 18-chlorin $p_6$ (13-carboxy-17-[2-carboxyethyl]-15-carboxy-17,18-trans-dihydro-3-vinyl-8-ethyl-2,7,12,18-tetramethylporphyrin)

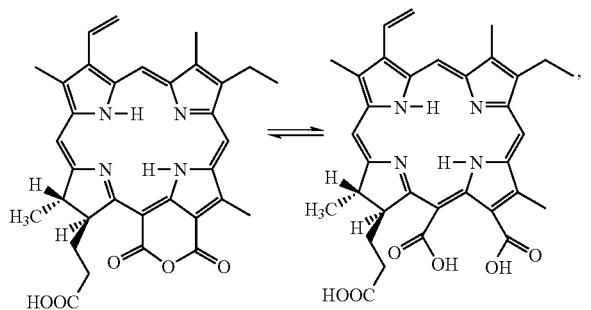

wherein the method comprising:
a. treating *Spirulina* biomass with acetone until chlorophyll a is completely extracted,
b. separating the extract by filtering or centrifuging the biomass,
c. treating the extract with acid in order to remove magnesium ion out of the chlorophyll molecule and to hydrolyse a phytyl ester group to form an acidic pheophytin a mixture
d. neutralizing the acidic pheophytin a mixture with a strong inorganic base, to precipitate pheophytin a which is then filtered,
e. hydrolyzing pheophytin a a mixture of hydrochloric acid-acetone-hexane with, 6-16 ml acetone, 0.6-6-ml hexane and 5-10 ml concentrated hydrochloric acid being used for every 1 g of crude pheophytin a,
f. heating the mixture up to 40-60° C. while stirring for a period of time from 20 minutes to 1 hour,
g. adding hexane (6-16 ml) to the mixture to form an organic phase and a water phase,
h. contacting the organic phase with a mixture of acetone and hydrochloric acid in a ratio from 2:1 to 10:1,
i. contacting the water phase that contains pheophorbide a with hexane,
j. then contacting the water phase containing pheophorbide a with an excess of sodium citrate (tri-, di- or monosubstituted) water solution to precipitate pheophorbide a,
k. filtering the precipitated pheophorbide a, washing the precipitate with water,
l. recrystallizing the precipitated pheophorbide a using an acetone-water mixture, and air drying until its weight becomes constant,
m. dissolving the pheophorbide a in acetone,
n. adding a strong inorganic base in the form of a water solution of 0.05-1.00% concentration, while stirring at 30-60° C. for 5-30 min,
o. adding additional strong inorganic base in the form of a water solution of 1-50% concentration to form a mixture,
p. heating the mixture of step o at 40-60° C. for 20-90 min,
q. neutralizing by adding diluted hydrochloric acid to precipitate chlorin $e_6$,
r. separating by centrifugation the chlorin $e_6$
s. washing the chlorin $e_6$ with distilled water until the acid reaction disappears,
t. recrystallizing the chlorin $e_6$ 55-80% with acetone to separate linear tetrapyrroles,
u. filtering the chlorin $e_6$ and washing with distilled water,
v. heating the chlorin $e_6$ in a sealed reservoir at a temperature of from 40-100° C. for a period of time from 1 hour to 30 days,
w. cooling the chlorin $e_6$ and adding a strong base solution until the pH is in the range from 7.5-8.5, and optionally gel-filtering the mixture,
x. adding diluted hydrochloric acid solution to the obtained solution until precipitation,
y. separating the precipitate by filtering or centrifugation, and
z. adding concentrated strong hydroxide solution until the pH is in the range from 7.0-8.5, to obtain the photosensitizer comprising 80-90% chlorin $e_6$, 2-15% purpurin 5 and purpurin 18-chlorin $p_6$.

* * * * *

UNITED STATES PATENT AND TRADEMARK OFFICE
CERTIFICATE OF CORRECTION

PATENT NO. : 7,550,587 B2
APPLICATION NO. : 11/171076
DATED : June 23, 2009
INVENTOR(S) : Andrei V. Reshetnikov et al.

It is certified that error appears in the above-identified patent and that said Letters Patent is hereby corrected as shown below:

In column 26, claim 1, line 47, after "the chlorin" replace "$e_6$ 55-80%" with --$e_6$ 55-80%--.

Signed and Sealed this

Twenty-ninth Day of September, 2009

David J. Kappos
*Director of the United States Patent and Trademark Office*